(12) United States Patent
Chen et al.

(10) Patent No.: US 12,398,239 B2
(45) Date of Patent: Aug. 26, 2025

(54) PAN-TACTIC CRYSTALLINE AND RECYCLABLE POLYTHIOESTERS

(71) Applicant: COLORADO STATE UNIVERSITY RESEARCH FOUNDATION, Fort Collins, CO (US)

(72) Inventors: Eugene Y. Chen, Fort Collins, CO (US); Changxia Shi, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 717 days.

(21) Appl. No.: 17/781,501

(22) PCT Filed: Dec. 2, 2020

(86) PCT No.: PCT/US2020/062837
§ 371 (c)(1),
(2) Date: Jun. 1, 2022

(87) PCT Pub. No.: WO2021/113325
PCT Pub. Date: Jun. 10, 2021

(65) Prior Publication Data
US 2023/0037920 A1 Feb. 9, 2023

Related U.S. Application Data

(60) Provisional application No. 62/943,520, filed on Dec. 4, 2019.

(51) Int. Cl.
*C08G 75/26* (2006.01)
*C07D 333/78* (2006.01)
*C07D 341/00* (2006.01)

(52) U.S. Cl.
CPC ........... *C08G 75/26* (2013.01); *C07D 333/78* (2013.01)

(58) Field of Classification Search
None
See application file for complete search history.

(56) References Cited

U.S. PATENT DOCUMENTS 3,640,965 A * 2/1972 Brode .................... C08G 75/12
528/196
4,219,658 A * 8/1980 Roman .................. A01N 53/00
549/52

(Continued)

OTHER PUBLICATIONS

Benassi et al., "A Convenient Synthesis of 2-Thiabicyclo[heptane and the Corresponding 1,4,5-endo,6-endo-7,7-Hexadeutero Derivative," Synthesis, 1974(10), pp. 735-736 (Year: 1974).*

(Continued)

*Primary Examiner* — Ha S Nguyen
(74) *Attorney, Agent, or Firm* — Haukaas Fortius PLLC; Michael Haukaas

(57) ABSTRACT

A monomer design strategy based on a bridged bicyclic thiolactone that produces stereo-disordered to perfectly stereo-ordered polythioesters is disclosed. The described polythioesters exhibit high crystallinity and full chemical recyclability. Such polymers possess intrinsic tacticity-independent crystallinity and chemical recyclability, tunable tacticities from stereo-disorder to perfect stereoregularity, as well as combined high-performance properties such as high thermal stability and crystallinity, and high mechanical strength, ductility and toughness.

16 Claims, 17 Drawing Sheets

(56) References Cited

U.S. PATENT DOCUMENTS 9,670,324 B2  6/2017  Rappoport et al.
2019/0040191 A1  2/2019  Chen et al.

OTHER PUBLICATIONS

Bannin et al., "Poly(thioester) by Organocatalytic Ring-opening polymerization," Macromolecules, 48, pp. 5481-5486, (2015) (Year: 2015).*

Yuan et al., "4-Hydroxyproline-Derived Sustainable Polythioesters: Controlled Ring-Opening Polymerization, Complete Recyclability, and Facile Functionalization," Journal of the American Chemical Society, 141, pp. 4928-4935 (2019) (Year: 2019).*

Bannin et al., "Poly(thioester by Organocatalytic Ring-Opening Polymerization" Macromolecules. Aug. 25, 2015, 48(16): 5481-5486.

Hong et al., "Chemically recyclable polymers: a circular economy approach to sustainability", Green Chem. 2017, 19, pp. 3692-3706.

Hong et al., "Completely recyclable biopolymers with linear and cyclic topologies via ring-opening polymerization of γ-butyrolactone", Nature Chemistry, vol. 8, Jan. 2016, pp. 42-49.

Hong et al., "Future Directions for Sustainable Polymers", Trends in Chemistry, May 2019, vol. 1, No. 2, pp. 148-151.

Hong et al., "Towards Truly Sustainable Polymers: A Metal-Free Recyclable Polyester from Biorenewable Non-Strained γ-Butyrolactone", Angew. Chem. Int. Ed. 2016, 55, pp. 4188-4193.

International Search Report and Written Opinion of the ISA/US dated Apr. 21, 2021 in International Application No. PCT/US2020/062837; 9pgs.

Lee et al., "Hydrogenated Ring-Opened Polynorbornene: A Highly Crystalline Atactic Polymer", Macromolecules, vol. 38, No. 4, 2005, pp. 1216-1222.

Mavila et al., "Dynamic and Responsive DNA-like Polymers", J. Am. Chem. Soc. 2018, 140, pp. 13594-13598.

Smith et al., "Radical Approach to Thioester-Containing Polymers", J. Am. Chem. Soc. 2019, 141, pp. 1446-1451.

Tang et al., "Stereosequenced crystalline polyhydroxyalkanoates from diastereomeric monomer mixtures", Nov. 8, 2019, Science 366, pp. 754-758.

Tang et al., "Toward Infintely Recyclable Plastics Derived from Renewable Cyclic Esters", Feb. 14, 2019, Chem 5, pp. 284-312.

Yuan et al., 4-Hydroxyproline-Derived Sustainable Polythioesters: Controlled Ring-Opending Polymerization, Complete Recyclability, and Facile Functionalization, J. Am. Chem. Soc. 2019, 141, pp. 4928-4935.

Zhu et al., "A synthetic polymer system with repeatable chemical recyclability", Apr. 27, 2018, Science 360, pp. 398-403.

Zhu et al., "Catalyst-Sidearm-Induced Stereoselectivity Switching in Polymerization of a Racemic Lactone for Stereocomplexed Crystalline Polymer with a Circular Life Cycle", Angew. Chem. Int. Ed. 2019, 58, pp. 1178-1182.

\* cited by examiner

E (3) Started (2) Recycled (1)

PAN-TACTIC CRYSTALLINE AND RECYCLABLE POLYTHIOESTERS

RELATED APPLICATIONS

This application is a National Stage filing under 35 U.S.C. § 371 of International Application No. PCT/US2020/062837 filed Dec. 2, 2020, which claims priority under 35 U.S.C. § 119 (e) to U.S. Provisional Patent Application No. 62/943,520 filed Dec. 4, 2019, which applications are incorporated herein by reference.

GOVERNMENT SUPPORT

This invention was made with government support under Grant No. DE-AC36-08GO28308 awarded by the Department of Energy. The government has certain rights in the invention.

BACKGROUND OF THE INVENTION

The failure to address end-of-life issues of today's plastics has not only accelerated depletion of finite natural resources, but also caused severe worldwide plastics pollution problems and resulted in enormous energy and materials value loss in the global economy. To address this global challenge, the design of next-generation polymers must consider their afterlife issues and establish closed-loop lifecycles towards a circular economy. In this context, the development of chemically recyclable polymers that can be depolymerized back to their monomer building-blocks in high selectivity and purity for virgin-quality polymer reproduction offers a circular economy approach to address these dire environmental and economic issues. For example, the ring-opening polymerization (ROP) of unstrained γ-butyrolactone (GBL) leads to polyester PGBL that can be completely depolymerized back to GBL in quantitative purity and yield with a low energy input. However, PGBL's performance properties are insufficient for common applications. To address this depolymerizability/performance tradeoff, ring-fused bicyclic GBL structural derivatives were designed to enhance monomer polymerizability as well as polymer thermal stability and crystallinity without compromising the full chemical recyclability, but the resulting crystalline materials with high melting-transition temperatures ($T_m$) are mechanically brittle, thus requiring incorporation of flexible copolymers to reach useful ductility.

In addition, to afford such crystalline materials demands either stereocomplexation of the preformed enantiomeric polymers from separate pools of enantiopure monomers or the elaborate stereoselective polymerization of the racemic monomer pool. When compared to the extensively studied ROP of lactones, the ROP of thiolactones has been examined to a much lesser extent. A significant development on that front is that the ROP of chiral N-substituted cis-4-thia-$_L$-proline thiolactones leads to polythioesters that are readily functionalizable (via the N site on the pyrrolidine ring) and show full chemical recyclability. However, the resulting polythioesters exhibit relatively low thermal stability with a $T_{d,5\%}$ (decomposition temperature at 5% weight loss) of ~200° C. and no observable $T_m$, despite their chiral structure, and dilute conditions (1.0 g polymer/100 mL solvent) were required to achieve their full chemical recyclability. The above examples highlight the daunting challenges of designing chemically recyclable polymers that exhibit combined desirable, but often conflicting, properties into one polymer structure, as they must overcome two types of tradeoffs: depolymerizability/performance and crystallinity/ductility.

For polymers containing stereogenic centers, there is also a stereo-disorder/crystallinity tradeoff that must be addressed. The stereochemical order or tacticity that measures the relative stereochemical arrangement or order of neighboring stereocenters located on their main-chain backbone of polymers significantly impacts their physical and mechanical properties. Although stereoregularity of polymers is neither a necessary nor a sufficient condition for their crystallinity, as a general rule for tactic polymers, tacticity determines their crystallinity; thus, high tacticity is required to pack polymer chains effectively into a (semi)crystalline domain. Therefore, higher tacticity leads to a crystalline polymer with a higher $T_m$, whereas stereo-disordered or atactic polymers having a random arrangement of stereocenters or even modestly tactic polymers are often amorphous. This long-standing rule highlights the importance of achieving a high degree of stereochemical control in polymer synthesis and often represent a highly demanding task for many polymerization systems, which has continuously challenged polymer chemists. However, there are few exceptions to this rule. For example, atactic poly(vinylene-cis-1,3-cyclopentylene) (fully hydrogenated polynorbornene, hPN) is unexpectedly crystalline, which is attributed to the unusual ability to crystallize with good three-dimensional order (a defined unit cell) even in the presence of a high degree of local structural disorder (configurational disorder in the cis-cyclopentylene rings). An obvious advantage of designing such tacticity-independent crystalline polymers is to circumvent the burden of developing exquisite stereoselective syntheses to achieve highly stereoregular, high-performance crystalline polymers.

Accordingly, there is a need for recyclable, tacticity-independent crystalline polymers that are derived from monomers with good polymerizability and have good mechanical properties.

SUMMARY

This disclosure provides a design for high-performance circular polymers with both intrinsic chemical recyclability and crystallinity. Guided by the following working hypotheses, we arrived at a bridged bicyclic thiolactone monomer, 2-thiabicyclo[2.2.1] heptan-3-one ([221]BTL), which can be prepared from a bio-based olefin carboxylic acid in 80% yield at a 50-g scale. First, [221]BTL should contain higher ring strain than the parent, non-polymerizable γ-thiobutyrolactone, which should allow the ROP to proceed at room temperature (RT) with high equilibrium monomer conversions and yield high molecular weight (MW) polymers. Second, the bridged bicyclic system should provide rigidity to the polymer backbone for enhanced thermal and mechanical properties. Third, the depolymerizability and selectivity in chemical recycling of the resulting polymer PBTL should be high since the ring-closure of the five-membered thiolactone is kinetically facile and thermodynamically favored. Furthermore, the bridged bicyclic monomer exists only in the cis-configuration, thus eliminating possible isomerization. Fourth, the aforementioned PBTL which also contains the cyclopentylene units—the motif leading to atactic yet crystalline hPN—could render its tacticity-independent, thus intrinsic, crystallinity, provided the unique ability to crystalize due to pseudo-symmetry and long-range order present in the pan-tactic PBTL with all degrees of tacticity.

Accordingly, this disclosure provides a polymer comprising a polythioester represented by Formula I:

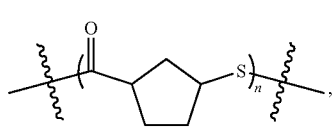

wherein
 the polythioester is a linear polythioester or a cyclic polythioester; and
 n is 20-50,000.

This disclosure also provides a method for forming the polymer above comprising:
 a1) contacting a bicyclic thiolactone monomer (M) and catalyst (Cat) to form a cyclic polythioester, wherein the catalyst is a metal-based catalyst or organic N-heterocyclic carbene (NHC); or
 a2) contacting the bicyclic thiolactone monomer, catalyst, and an initiator to form a linear polythioester, wherein the catalyst is an organic base and the pKa of the organic base is about 12 to about 42;
 wherein the monomer undergoes a polymerization reaction; and
 b) quenching the polymerization reaction in step a1) or step a2);
 wherein the ratio of M and Cat expressed as a ratio of their concentrations [M]/[Cat] is about 100/1 or greater, and the polymer is thereby formed.

The invention provides novel polymers of Formula I, Ii, IIA-IID, IIAi-IIDi, IIIA and IIIB, intermediates for the synthesis of polymers of the Formulas, as well as methods of preparing polymers of the Formulas. The invention also provides polymers of the Formulas that are useful as intermediates for the synthesis of other useful polymers.

The invention provides for the use of the compositions described herein for use in preparing or manufacturing various polymers.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
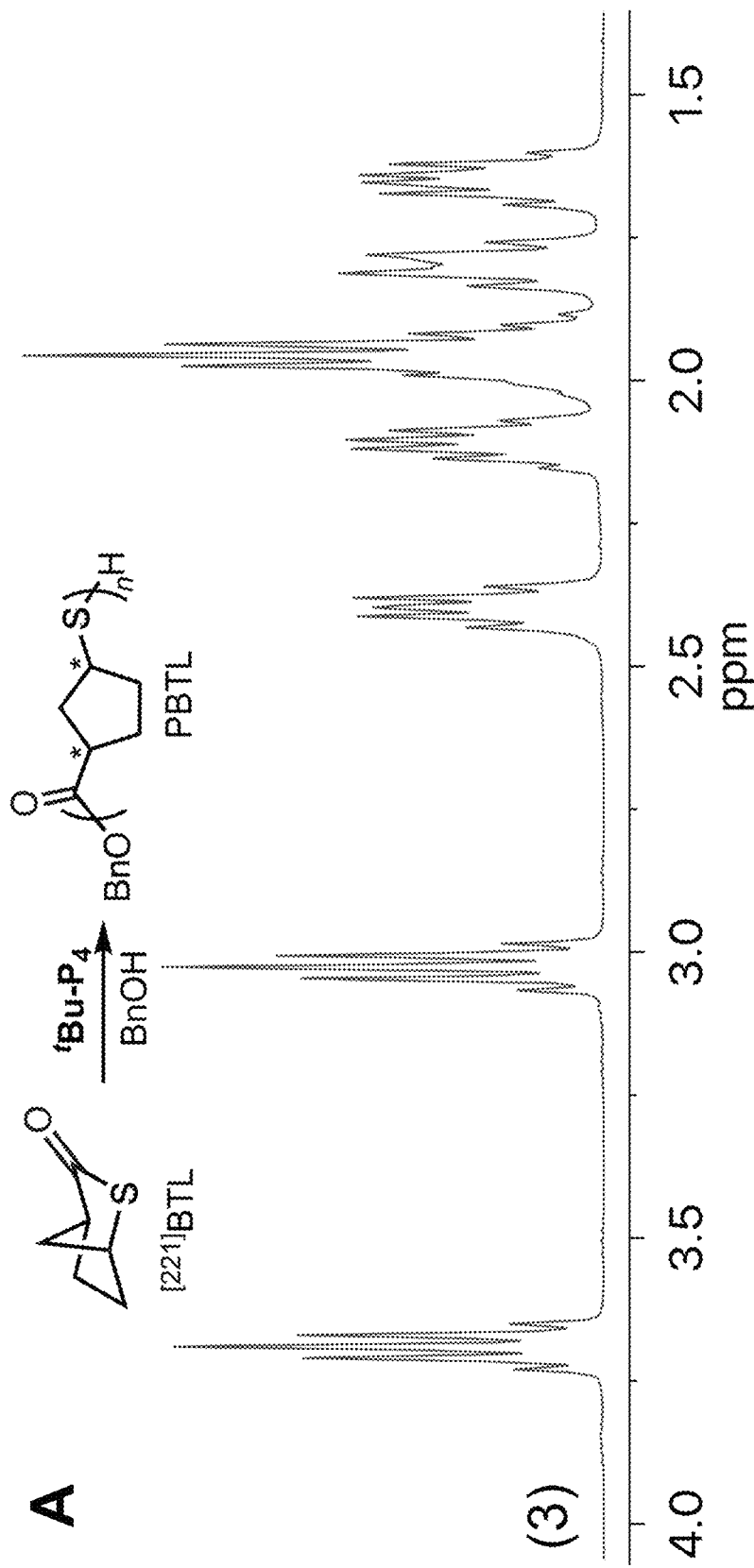
FIG. 1. NMR spectra and DSC thermograms of PBTL with varied stereoregularity. (A), $^1$H NMR (25° C., CDCl$_3$) spectra. (B), $^{13}$C NMR (25° C., CDCl$_3$) spectra in the C=O region. (C), DSC curves of second heating scans at 10° C./min. PBTL samples: (1) PBTL with low (32%) tacticity by DBU; (2) PBTL with medium (45%) tacticity by IMes; (3) PBTL with perfect (100%) tacticity by $^t$Bu-P$_4$.
Figure 1:
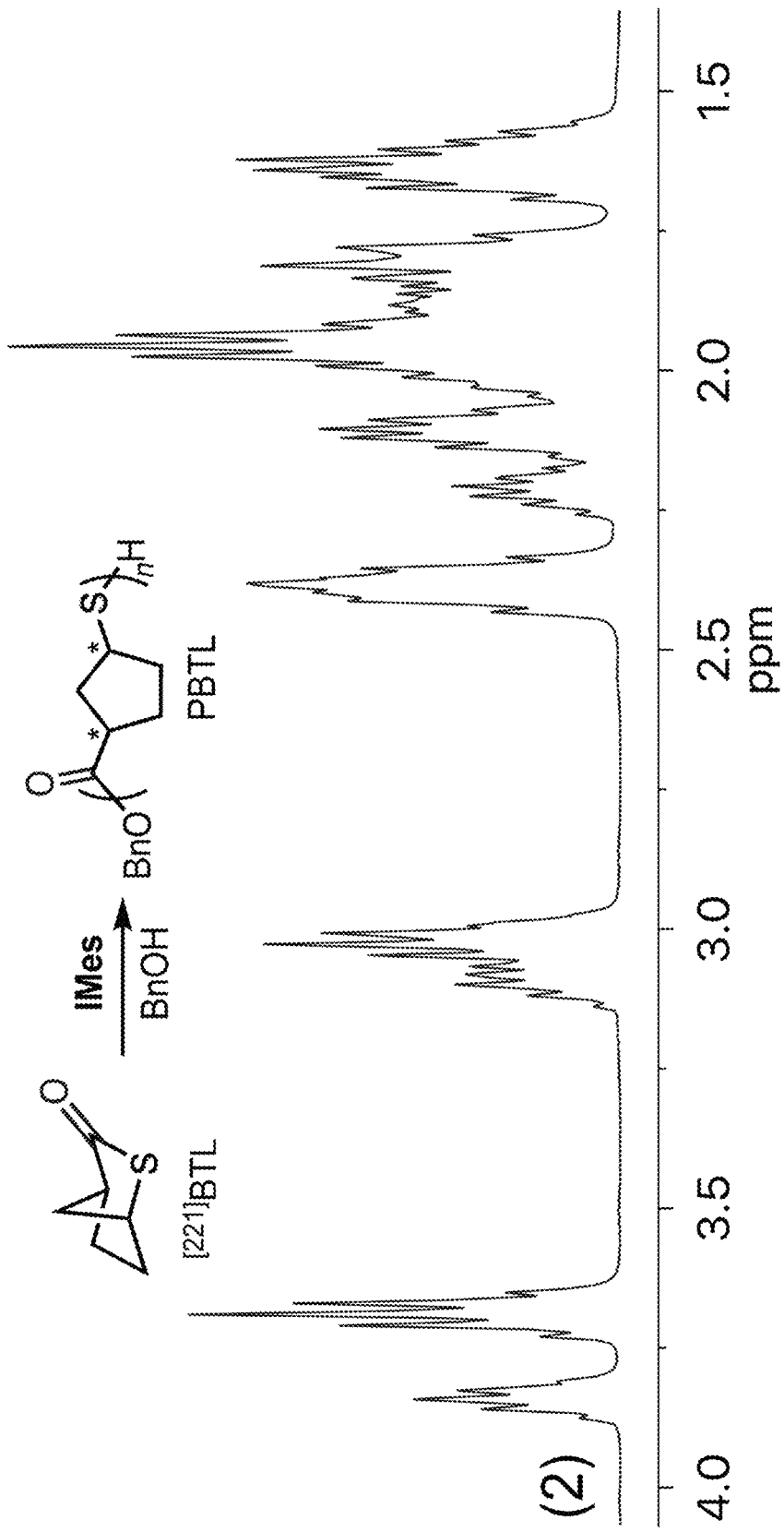
Figure 1:
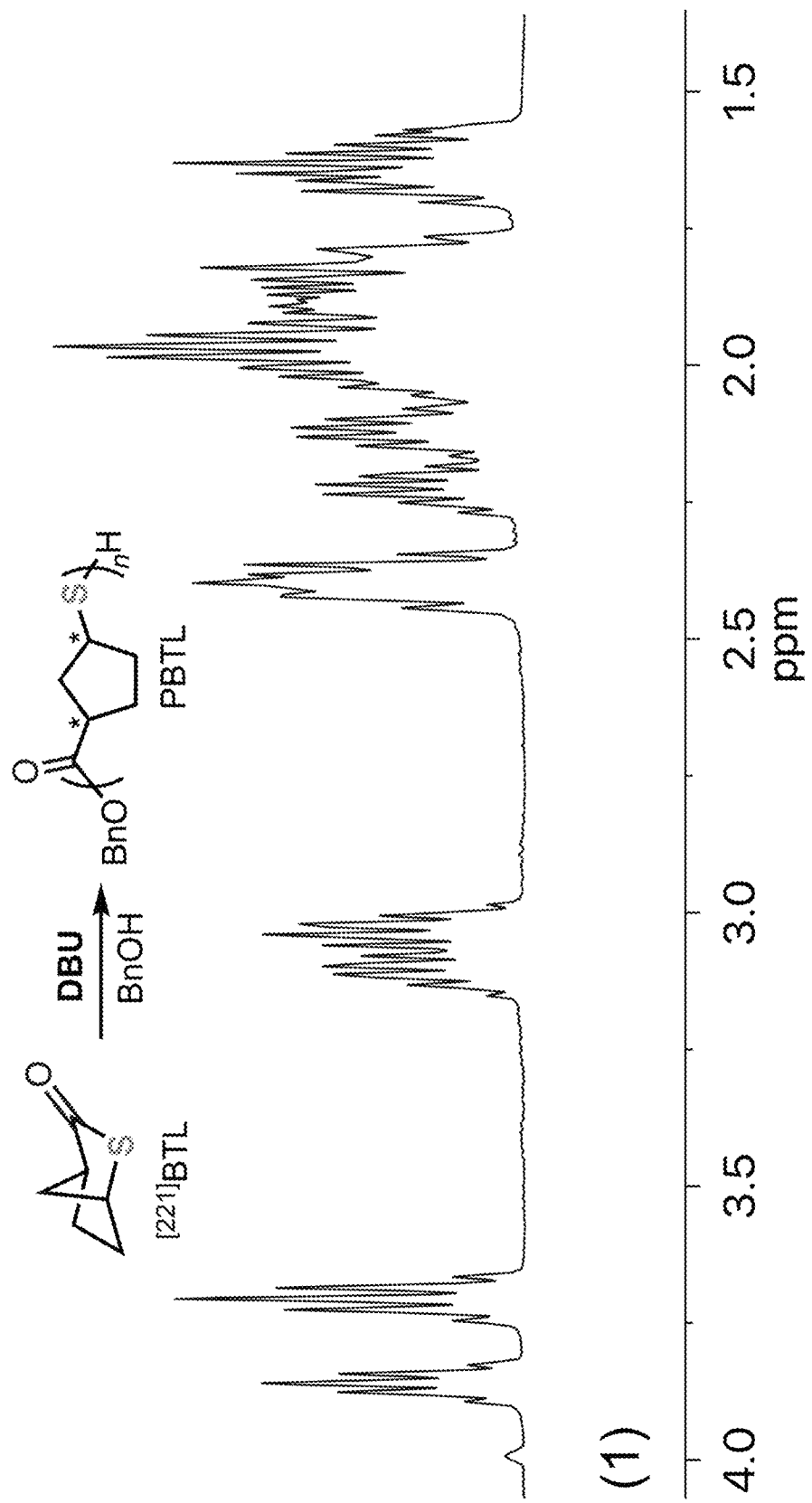
Figure 1:
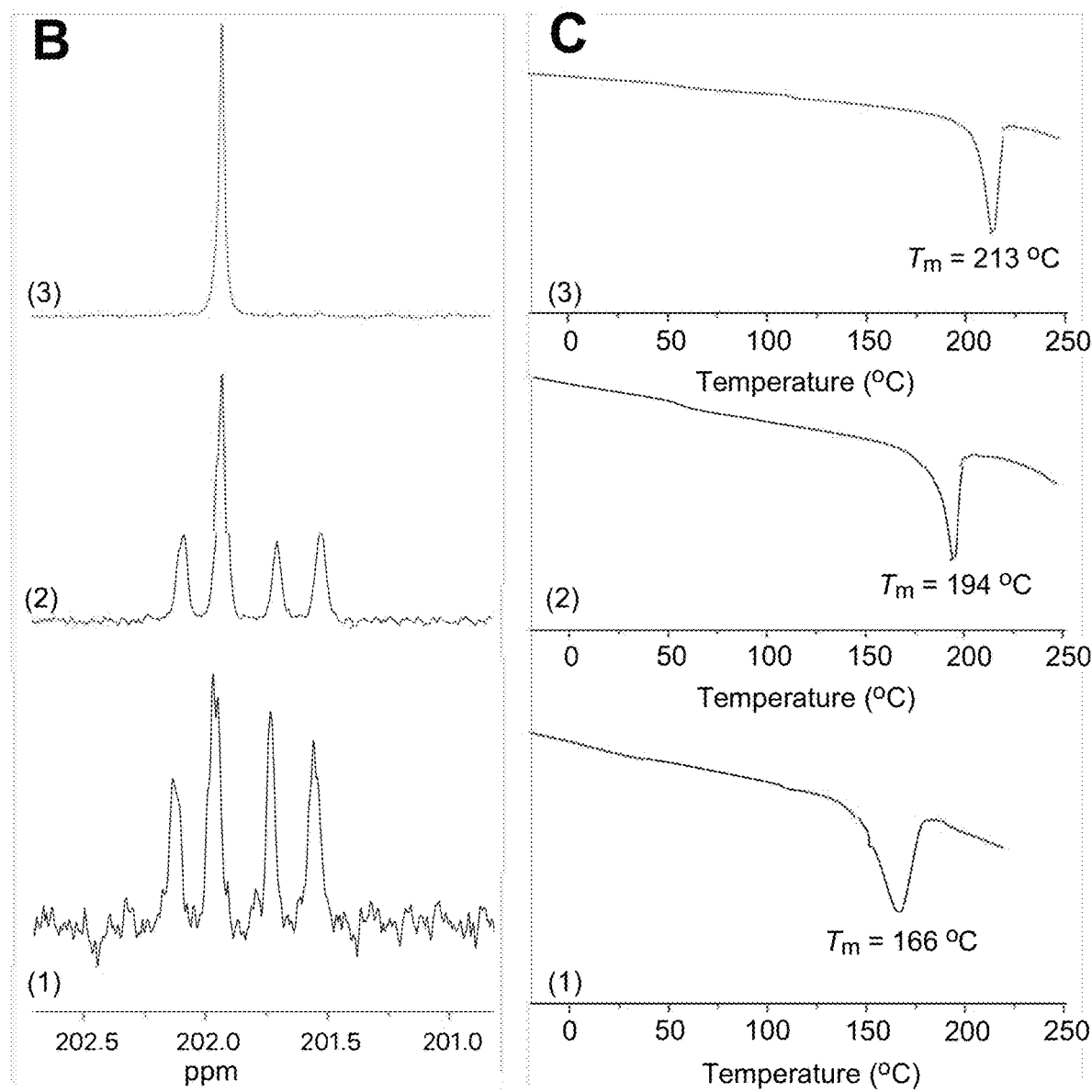

Three types of seemingly unyielding tradeoffs have continued to challenge the rational design for circular polymers with both high chemical recyclability and high-performance properties: depolymerizability/performance, crystallinity/ductility, and stereo-disorder/crystallinity (Scheme 1). Here we introduce a monomer design strategy based on a bridged bicyclic thiolactone that produces stereo-disordered to perfectly stereo-ordered polythiolactones, all exhibiting high crystallinity and full chemical recyclability. Such polythioesters defy aforementioned tradeoffs by possessing an unusual set of desired properties, including intrinsic tacticity-independent crystallinity and chemical recyclability, tunable tacticities from stereo-disorder to perfect stereoregularity, as well as combined high-performance properties such as high thermal stability and crystallinity, and high mechanical strength, ductility and toughness.

Scheme 1. Comparison of polymer properties obtained from bicyclic lactone (BL) and bicyclic thiolactone (BTL) monomers.

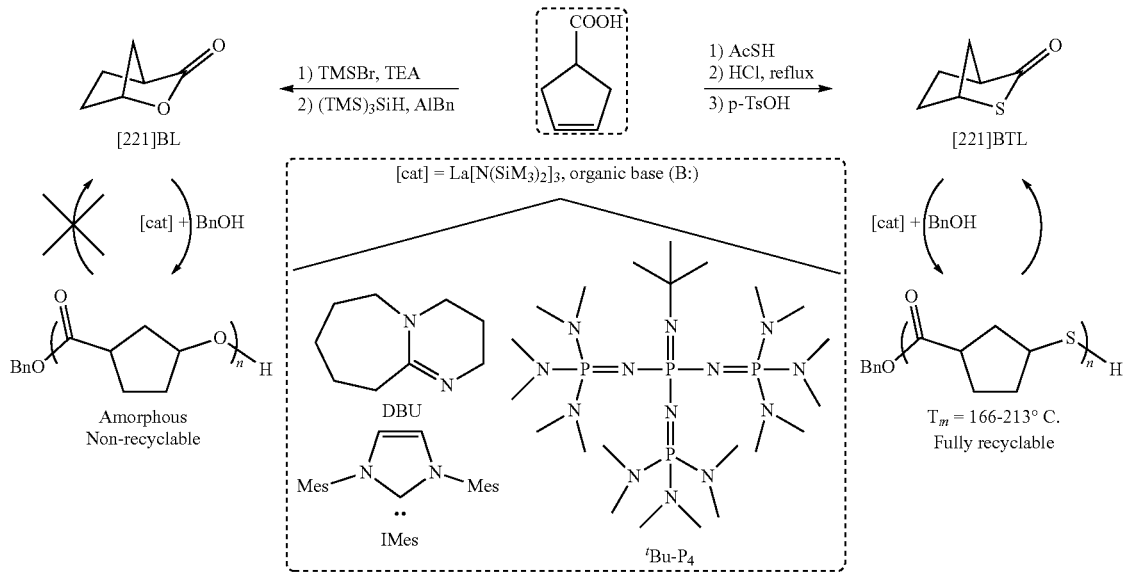

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The terms "about" and "approximately" are used interchangeably. Both terms can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the terms "about" and "approximately" are intended to include values, e.g., weight percentages, proximate to the recited range that are equivalent in terms of the functionality of the individual ingredient, composition, or embodiment. The terms "about" and "approximately" can also modify the end-points of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

This disclosure provides ranges, limits, and deviations to variables such as volume, mass, percentages, ratios, etc. It is understood by an ordinary person skilled in the art that a range, such as "number1" to "number2", implies a continuous range of numbers that includes the whole numbers and fractional numbers. For example, 1 to 10 means 1, 2, 3, 4, 5, . . . 9, 10. It also means 1.0, 1.1, 1.2. 1.3, . . . , 9.8, 9.9, 10.0, and also means 1.01, 1.02, 1.03, and so on. If the variable disclosed is a number less than "number10", it implies a continuous range that includes whole numbers and fractional numbers less than number10, as discussed above. Similarly, if the variable disclosed is a number greater than "number10", it implies a continuous range that includes whole numbers and fractional numbers greater than number10. These ranges can be modified by the term "about", whose meaning has been described above.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at molecular level, for example, to bring about a chemical reaction, or a physical change, e.g., in a solution, in a reaction mixture.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "substantially" as used herein, is a broad term and is used in its ordinary sense, including, without limitation, being largely but not necessarily wholly that which is specified. For example, the term could refer to a numerical value that may not be 100% the full numerical value. The full numerical value may be less by about 1%, about 2%, about 3%, about 4%, about 5%, about 6%, about 7%, about 8%, about 9%, about 10%, about 15%, or about 20%.

Wherever the term "comprising" is used herein, options are contemplated wherein the terms "consisting of" or "consisting essentially of" are used instead. As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein may be suitably practiced in the absence of any element or elements, limitation or limitations which is not specifically disclosed herein.

This disclosure provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in Compendium of Organic Synthetic Methods (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as March's Advanced Organic Chemistry: Reactions, Mechanisms, and Structure, 5th Ed., by M. B. Smith and J. March (John Wiley & Sons, New York, 2001); Comprehensive Organic Synthesis. Selectivity, Strategy & Efficiency in Modern Organic Chemistry. In 9 Volumes, Barry M. Trost, Editor-in-Chief (Pergamon Press, New York, 1993 printing); Advanced Organic Chemistry, Part B: Reactions and Synthesis, Second Edition, Cary and Sundberg (1983); for heterocyclic synthesis see Hermanson, Greg T., Bioconjugate Techniques, Third Edition, Academic Press, 2013.

The formulas and compounds described herein can be modified using protecting groups. Suitable amino and carboxy protecting groups are known to those skilled in the art (see for example, Protecting Groups in Organic Synthesis, Second Edition, Greene, T. W., and Wutz, P. G. M., John Wiley & Sons, New York, and references cited therein; Philip J. Kocienski; Protecting Groups (Georg Thieme Verlag Stuttgart, New York, 1994), and references cited therein); and Comprehensive Organic Transformations, Larock, R. C., Second Edition, John Wiley & Sons, New York (1999), and referenced cited therein.

The term "halo" or "halide" refers to fluoro, chloro, bromo, or iodo. Similarly, the term "halogen" refers to fluorine, chlorine, bromine, and iodine.

The term "alkyl" refers to a branched or unbranched hydrocarbon having, for example, from 1-20 carbon atoms, and often 1-12, 1-10, 1-8, 1-6, or 1-4 carbon atoms; or for example, a range between 1-20 carbon atoms, such as 2-6, 3-6, 2-8, or 3-8 carbon atoms. As used herein, the term "alkyl" also encompasses a "cycloalkyl".

As used herein, the term "substituted" or "substituent" is intended to indicate that one or more (for example, in various embodiments, 1-10; in other embodiments, 1-6; in some embodiments 1, 2, 3, 4, or 5; in certain embodiments, 1, 2, or 3; and in other embodiments, 1 or 2) hydrogens on the group indicated in the expression using "substituted" (or "substituent") is replaced with a selection from the indicated group(s), or with a suitable group known to those of skill in the art, provided that the indicated atom's normal valency is not exceeded, and that the substitution results in a stable compound. Suitable indicated groups include, e.g., alkyl, alkenyl, alkynyl, alkoxy, haloalkyl, hydroxyalkyl, aryl, heteroaryl, heterocyclyl, cycloalkyl, alkanoyl, alkoxycarbonyl, amino, alkylamino, dialkylamino, carboxyalkyl, alkylthio, alkylsulfinyl, and alkylsulfonyl.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof, such as racemic mixtures, which form part of the present invention.

A "solvent" as described herein can include water or an organic solvent. Examples of organic solvents include hydrocarbons such as toluene, xylene, hexane, and heptane; chlorinated solvents such as methylene chloride, chloroform, and dichloroethane; ethers such as diethyl ether, tetrahydrofuran, and dibutyl ether; ketones such as acetone and 2-butanone; esters such as ethyl acetate and butyl acetate; nitriles such as acetonitrile; alcohols such as methanol, ethanol, and tert-butanol; and aprotic polar solvents such as N,N-dimethylformamide (DMF), N,N-dimethylacetamide (DMA), and dimethyl sulfoxide (DMSO). Solvents may be used alone or two or more of them may be mixed for use to provide a "solvent system".

The term, "repeat unit", "repeating unit", or "block" as used herein refers to the moiety of a polymer that is repetitive. The repeat unit may comprise one or more repeat units, labeled as, for example, repeat unit A, repeat unit B, repeat unit C, etc. Repeat units A-C, for example, may be covalently bound together to form a combined repeat unit. Monomers or a combination of one or more different monomers can be combined to form a (combined) repeat unit of a polymer or copolymer.

The term "molecular weight" for the copolymers disclosed herein refers to the average number molecular weight (Me). The corresponding weight average molecular weight ($M_w$) can be determined from other disclosed parameters by methods (e.g., by calculation) known to the skilled artisan.

Embodiments of the Invention

This disclosure provides a polymer comprising a polythioester represented by Formula II:

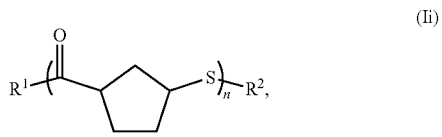

wherein
$R^1$ and $R^2$ are each independently a terminal group for a linear polythioester; or
$R^1$ and $R^2$ taken together form a cyclic polythioester; and
n is 20-50,000.

In some embodiments, the polythioester is a linear polythioester. In various embodiments, the ends of a polymer (i.e., the initiator end or terminal end), is a low molecular weight moiety (e.g. under 500 Da), such as, H, CN, SR, OR, OOR, $CH_2OR$, $NR_2$ wherein R is independently H or alkyl, or a hydrocarbon such as an alkyl (for example, a butyl or 2-cyanoprop-2-yl moiety at the initiator and terminal end), alkene or alkyne, or a moiety as a result of an elimination reaction at the first and/or last repeat unit in the polymer. In various other embodiments, $R^1$ and $R^2$ are each independently different polymers.

In some embodiments, the polythioester is a tactic polythioester. In some embodiments, the tactic polythioester has at least 20% tacticity. In some embodiments, the tactic polythioester has at least 90% tacticity. In some embodiments, the tactic polythioester comprises diads. In some embodiments, the tactic polythioester consists essentially of diads.

In other embodiments, the polythioester of Formula I is represented as one of Formula IIAi-IIDi:

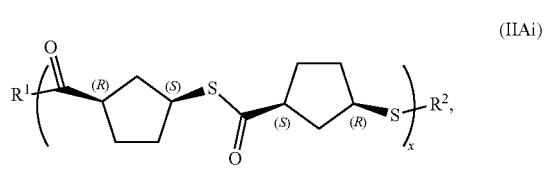

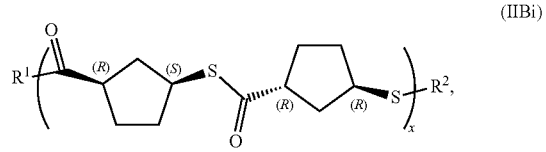

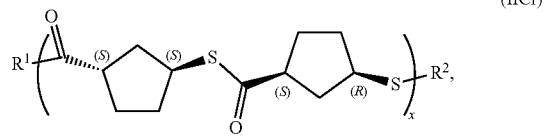

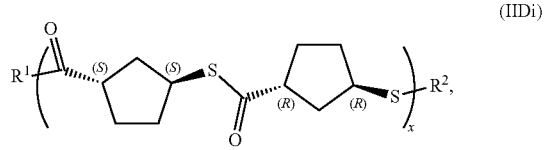

or an enantiomer thereof; wherein x is 10-25,000.

In some other embodiments, the polythioester is the threodisyndiotactic polymer of Formula IIA or the erythrodisyndiotactic polymer of Formula IID. In some embodiments, the polythioester is a cyclic polythioester.

In other embodiments, the cyclic polythioester is represented as Formula IIIA or IIIB:

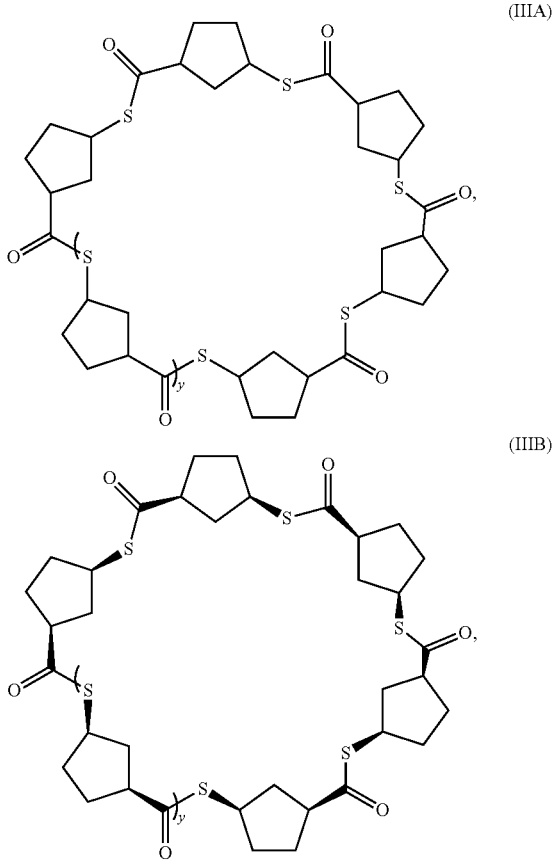

or a stereoisomer or enantiomer thereof, wherein y is 0-10,000.

Also, this disclosure provides a composition comprising a bicyclic thiolactone monomer (M) and a catalyst (Cat) wherein the catalyst is a metal-based catalyst, organic N-heterocyclic carbene (NHC), or organic base and the pKa of the organic base is about 12 to about 42.

In some embodiments, the monomer is 2-thiabicyclo[2.2.1]heptan-3-one ([221]BTL). In some embodiments, the composition comprises an NHC and the NHC is 1,3-bis(2,4,6-trimethylphenyl) imidazol-2-ylidene (IMes).

In some other embodiments, the composition comprises the metal-based catalyst and the catalyst is tris[N,N-bis(trimethylsilyl)amide]lanthanum(III) (La—N); or the composition comprises the organic base and the organic base is 1,8-diazabicyclo[5.4.0]undec-7-ene (DBU), or 1-tert-butyl-4,4,4-tris(dimethylamino)-2,2-bis[tris(dimethylamino)-phosphoranylid-enamino]-2$\lambda^5$,4$\lambda^5$-catenadi (phosphazene) ($^t$Bu-P$_4$). In other embodiments, the ratio of M and Cat expressed as a ratio of their concentrations [M]/[Cat] is about 100/1 or greater.

Additionally, this disclosure provides a method for forming the polymer disclosed herein comprising:

a1) contacting a bicyclic thiolactone monomer (M) and catalyst (Cat) to form a cyclic polythioester, wherein the catalyst is a metal-based catalyst or organic N-heterocyclic carbene (NHC); or a2) contacting the bicyclic thiolactone monomer, catalyst, and an initiator to form a linear polythioester, wherein the catalyst is an organic base and the pKa of the organic base is about 12 to about 42;

wherein the monomer undergoes a polymerization reaction; and b) quenching the polymerization reaction in step a1) or step a2);

wherein the ratio of M and Cat expressed as a ratio of their concentrations [M]/[Cat] is about 100/1 or greater, and the polymer is thereby formed.

In various embodiments, the bicyclic thiolactone monomer is 2-thiabicyclo[2.2.1] heptan-3-one ([221]BTL).

In additional embodiments, the method comprises step a1) and step b) and the catalyst is tris [N,N-bis(trimethylsilyl)amide]lanthanum(III) (La—N) or 1,3-bis(2,4,6-trimethylphenyl) imidazol-2-ylidene (IMes); or the method comprises step a2) and step b) and the catalyst is 1,8-diazabicyclo[5.4.0]undec-7-ene (DBU), tris[N,N-bis(trimethylsilyl)amide]lanthanum (III) (La—N), or 1-tert-butyl-4,4,4-tris(dimethylamino)-2,2-bis[tris(dimethylamino)-phosphoranylid-enamino]-2$\lambda^5$,4$\lambda^5$-catenadi (phosphazene) ($^t$Bu-P$_4$), and the initiator is an alcohol.

In some other embodiments, the polymer formed is crystalline and has a melting transition temperature ($T_m$) of about 150° C. to about 250° C.

In yet other embodiments, the above method further comprises depolymerizing the formed polymer to the parent bicyclic thiolactone monomer wherein the formed polymer and a catalyst are contacted at about 10° C. to about 200° C., thereby depolymerizing the formed polymer.

Furthermore, this disclosure provides a method for depolymerizing a polythioester comprising contacting the polythioester disclosed herein and a catalyst at about 10° C. to about 120° C., wherein the polythioester is depolymerized to the parent bicyclic thiolactone monomer wherein the parent is 2-thiabicyclo[2.2.1]heptan-3-one ([221]BTL).

Results and Discussion

Control of tacticity, crystallinity and topology. The results of the ROP of racemic [221]BTL by four different catalyst/initiator systems were summarized in Table 1. First, with the La—N/BnOH system, the ROP in toluene at RT with [M]/[La—N]/[BnOH]=300/1/3 achieved only 57% conversion after 24 h {La—N=La[N(SiMe$_3$)$_2$]$_3$; BnOH=benzyl alcohol, which converts in situ the La—N precatalyst to the La-OBn catalyst via facile alcoholysis; M=monomer}. Although the resulting PBTL has a low number-average MW (Mn) of 8.8×10$^3$ g mol$^{-1}$ and is not stereoregular based on $^1$H and $^{13}$C NMR spectra, it unexpectedly is crystalline with a high $T_m$ of 167° C. (FIG. 1) and heat of fusion ($\Delta H_f$) of 25.6 J g$^{-1}$ measured by differential scanning calorimetry (DSC) from a second heating scan at 10° C./min. Likewise, the ROP catalyzed by organic base 1,8-diazabicyclo[5.4.0]

undec-7-ene (DBU) led to atactic PBTL but is semi-crystalline, exhibiting a $T_m$ of 166° C. The use of superbase 1-tert-butyl-4,4,4-tris(dimethylamino)-2,2-bis[tris(dimethylamino)-phosphoranylid-enamino]-2$\lambda^5$,4$\lambda^5$-catenadi (phosphazene) ($^t$Bu-P$_4$) resulted in immediate gelation with a M concentration of 160 mg/0.1 mL in toluene, affording also a crystalline PBTL but with a higher $T_m$ of 176° C., while still being mostly atactic.

Figure 2:
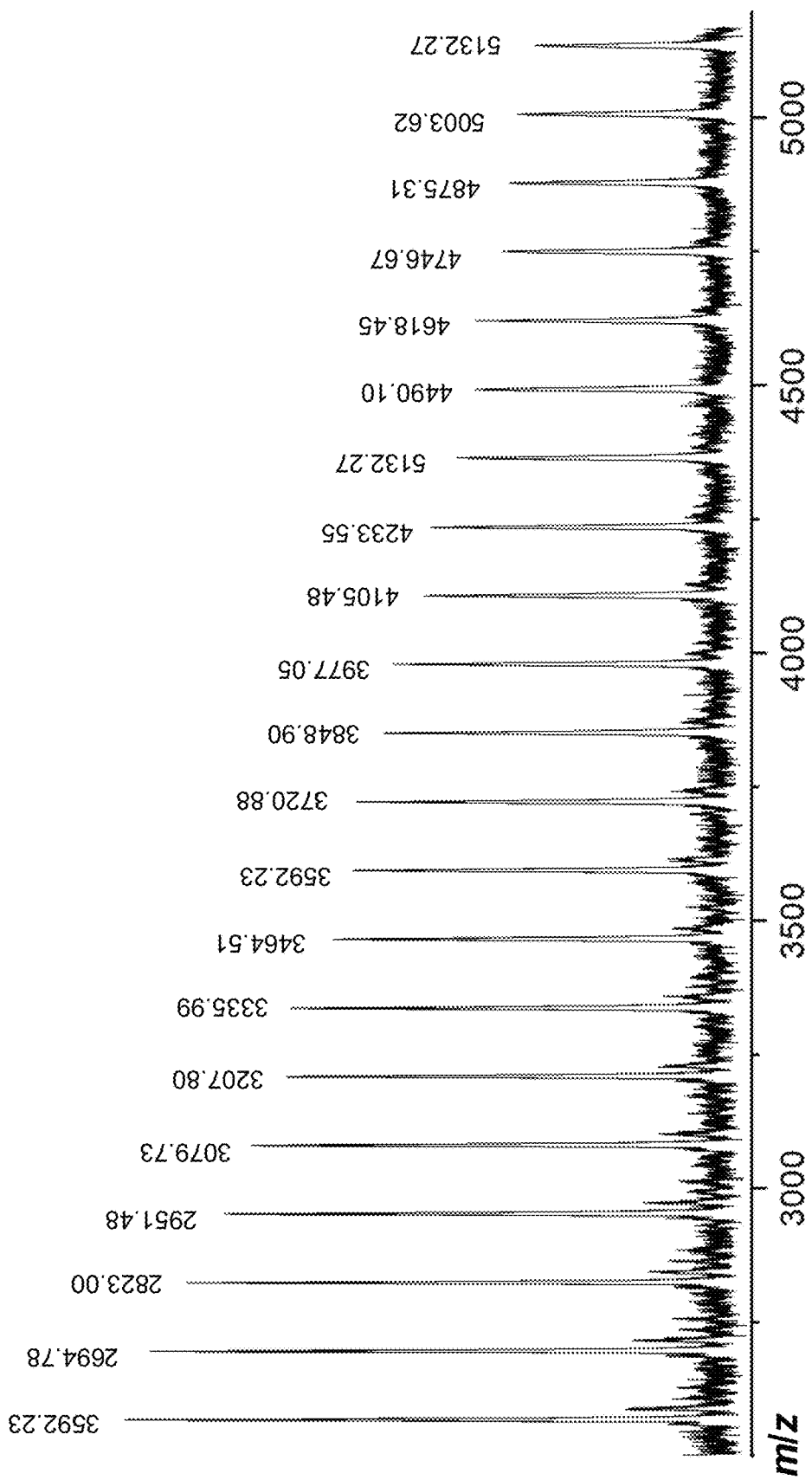
FIG. 2. Determination of topology by MALDI-TOF MS and viscosity. (A), MS spectrum and plot of m/z values versus the theoretical number of M repeat units for the linear PBTL produced by IMes+BnOH. (B), MS spectrum and plot of m/z values versus the theoretical number of M repeat units for the cyclic PBTL produced by IMes alone. (C), Double logarithm (Mark-Houwink) plots of intrinsic viscosity [η] vs. M$_w$ of the linear (blue line) and cyclic (red line) PBTL samples produced by IMes with BnOH and without BnOH. Inset: a photograph of isolated cyclic PBTL.
Figure 2:
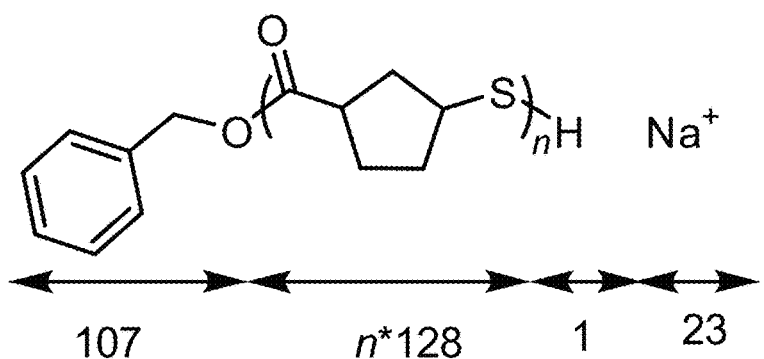
Figure 2:
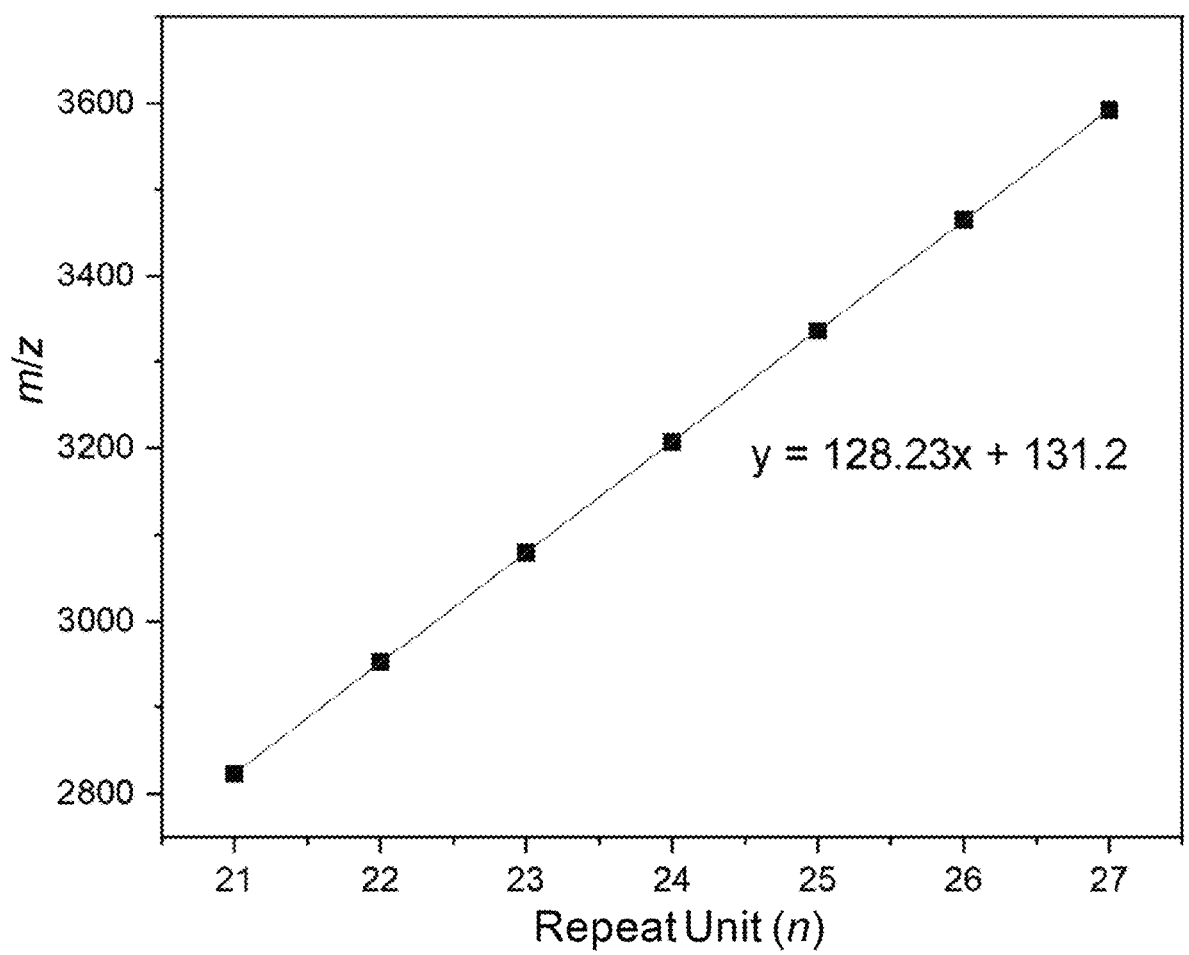
Figure 2:
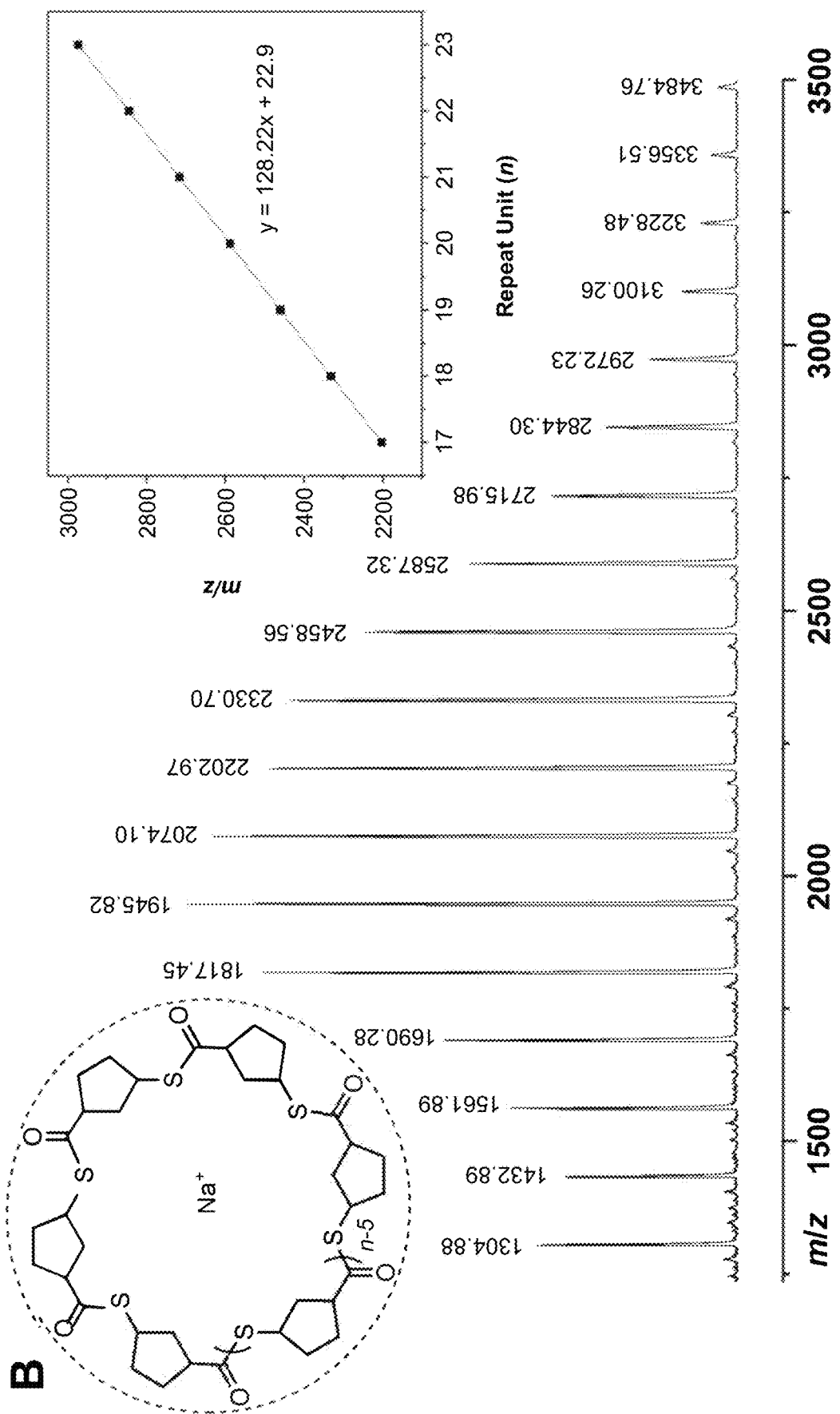
Figure 2:
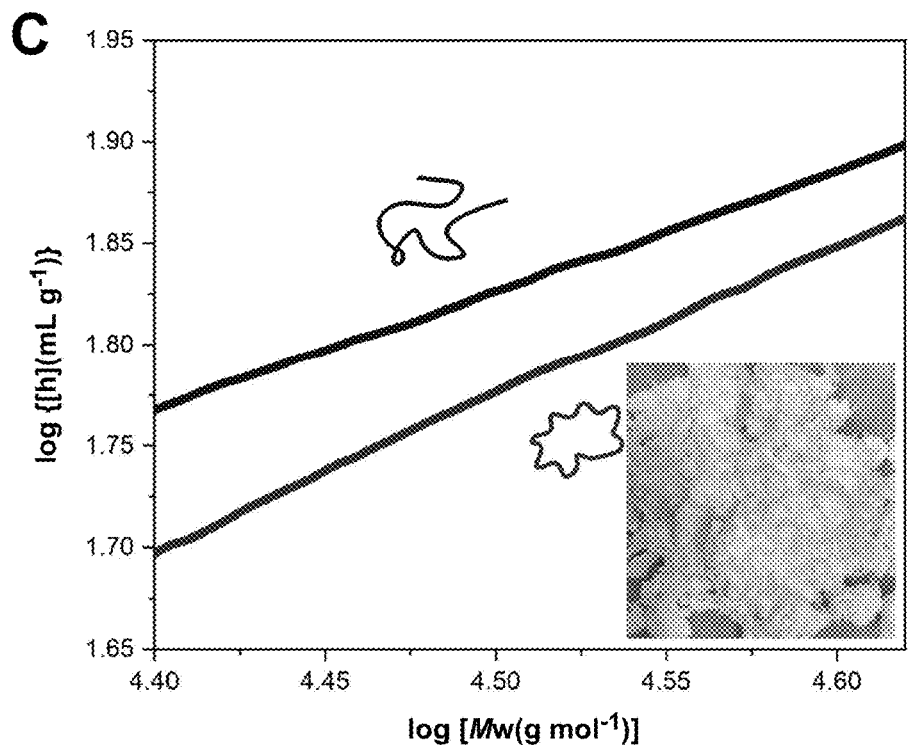

Intriguingly, when the M concentration was increased to 240 mg/0.1 mL in toluene and the catalyst loading was decreased to reach a ratio of [M]/[$^t$Bu-P$_4$]/[BnOH]=1000/1/1, the $T_m$ of the resulting PBTL ($M_n$=4.98×10$^4$ gmol$^{-1}$, Đ=1.44) increased significantly to 213° C. [glass-transition temperature ($T_g$)=112° C.], coupled with essentially perfect stereoregularity as revealed by its $^{13}$C NMR (Table 1, run 4; FIG. 1B). Replacing $^t$Bu-P$_4$ with a N-heterocyclic carbene (NHC), 1,3-bis(2,4,6-trimethylphenyl) imidazol-2-ylidene (IMes), the ROP with [M]/[IMes]/[BnOH]=1000/1/1 (320 mg M in 0.1 mL toluene) reached 85% in 5 min, affording a high MW, crystalline PBTL ($M_n$=1.15×10$^5$ g mol$^{-1}$, $T_m$=194° C., FIG. 1C). By gradually lowering the IMes catalyst loading to 0.02%, we realized essentially perfectly stereoregular PBTL with $T_m$=213° C. The linear structure of the PBTL produced by the catalyst/BnOH systems was characterized by the end groups from their NMR spectra, which was further confirmed by matrix-assisted laser desorption/ionization-time-of-flight mass spectrometry (MALDI-TOF MS) to show the linear structure BnO-{[221]BTL}$_n$-H (FIG. 2A).

As NHCs are well established catalysts promoting cyclic polymer formation through zwitterionic ROP of lactones and lactides, we performed zwitterionic ROP of [221]BTL using IMes in toluene at RT. The ROP with [M]/[IMes] =100/1 (160 mg M in 0.1 mL toluene) gelled in 10 s and reached 44% conversion, with a final conversion of 72% upon quenching after 5 min. This resultant PBTL ($M_n$=6.61× 10$^4$ g mol$^{-1}$, Đ=2.37) is also a crystalline material, showing a $T_m$ of 176° C. (Table 2, run 1). Analysis of a low-MW sample by MALDI-TOF MS (FIG. 2B) revealed no end groups, indicating that IMes mediated zwitterionic ROP to produce cyclic PBTL. To provide further experimental evidence to distinguish between the linear and cyclic PBTL topologies, GPC with light scattering, refractive index, and viscosity triple detection was utilized to analyze and compare the PBTL materials produced by IMes with (to linear PBTL) or without (to cyclic PBTL) the BnOH initiator. A Mark-Houwink plot (i.e., double logarithmic plots of intrinsic viscosity [η] vs. $M_w$ determined by light scattering detection) of the linear PBTL produced by IMes/BnOH (Table 1, run 6) and the cyclic PBTL produced by IMes alone (Table 2, run 6) is depicted in FIG. 2C. As expected, cyclic PBTL exhibited a lower intrinsic viscosity than its linear analog, with a [η]$_{cyclic}$/[η]$_{linear}$ ratio of approximately 0.7, consistent with the theoretically predicted value for cyclic polymers.

Subsequent studies examined effects on the polymerization characteristics and cyclic PBTL properties (particularly $M_n$ and $T_m$) by varying the [M]/[IMes] ratio (100/1 to 1000/1), M concentration (1.60 to 3.20 g/mL), and solvent polarity (toluene, THF, DMF). From the results summarized in Table 2, several trends can be observed. First, these polymerizations typically gel in a few seconds and are not well-controlled, affording high MW, crystalline cyclic PBTL with even a relatively low [M]/[IMes] ratio to 300/1: $M_n$=1.70×10$^5$ g mol$^{-1}$, Đ=2.78, and $T_m$=180° C. Second, employing combined high M concentration (2.40 g/mL) and high [M]/[IMes] ratio (1000/1) conditions produced cyclic PBTL with essentially perfect tacticity, as characterized by the highest $T_m$ of 213° C. and $^{13}$C NMR spectra. Third, changing the solvent from toluene to THF, while employing high M concentration and [M]/[IMes] ratio conditions, can also lead to perfectly tactic cyclic PBTL, but the ROP in the most polar solvent of this series (DMF) led to erosion of tacticity to only 30% (vide infra).

Figure 3:
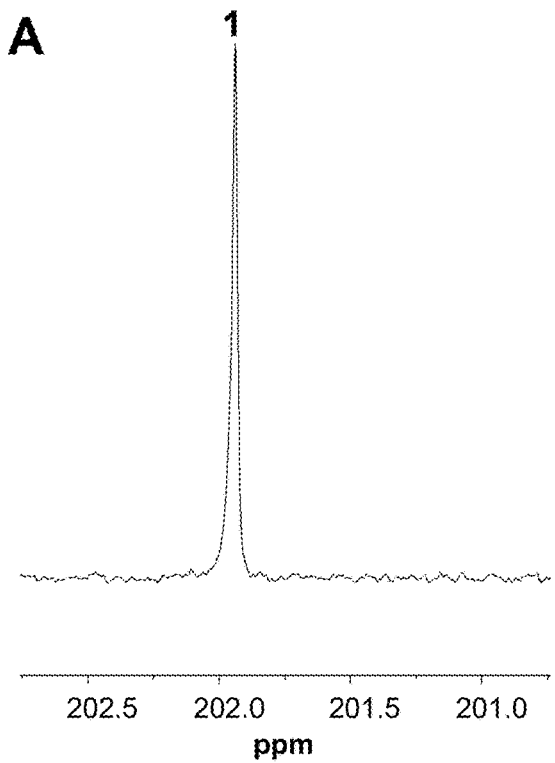
FIG. 3. Assignments of stereomicrostructures of PBTL and $^{13}$C NMR spectra. (A), PBTL produced by IMes (Table 2, run 8). (B), PBTL produced by DBU (Table 1, run 2). (C), PBTL produced by IMes (Table 1, run 8). (D), PBTL produced by $^t$Bu-P$_4$, [M]/[$^t$Bu-P$_4$]/[BnOH]=100/1/1, 0.80 g/mL.
Figure 3:
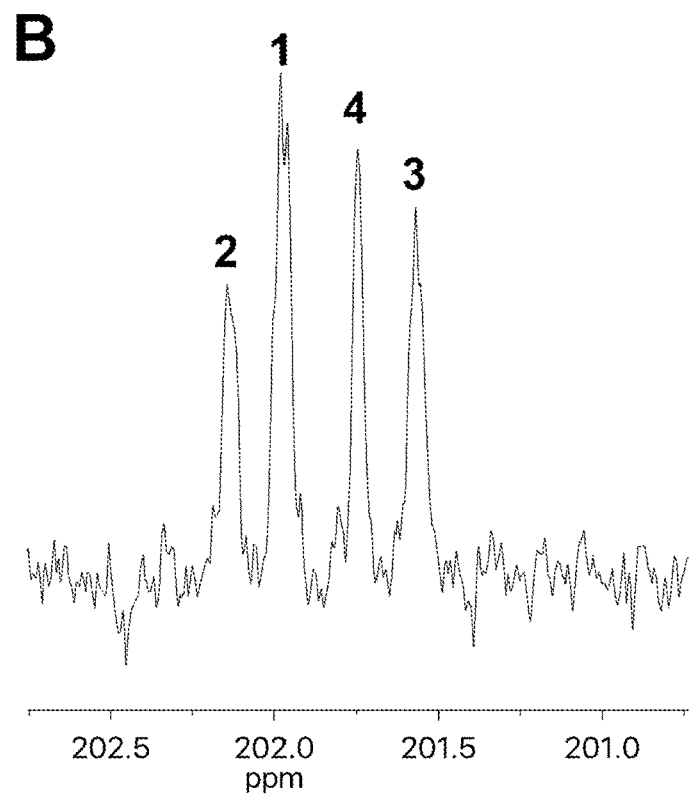
Figure 3:
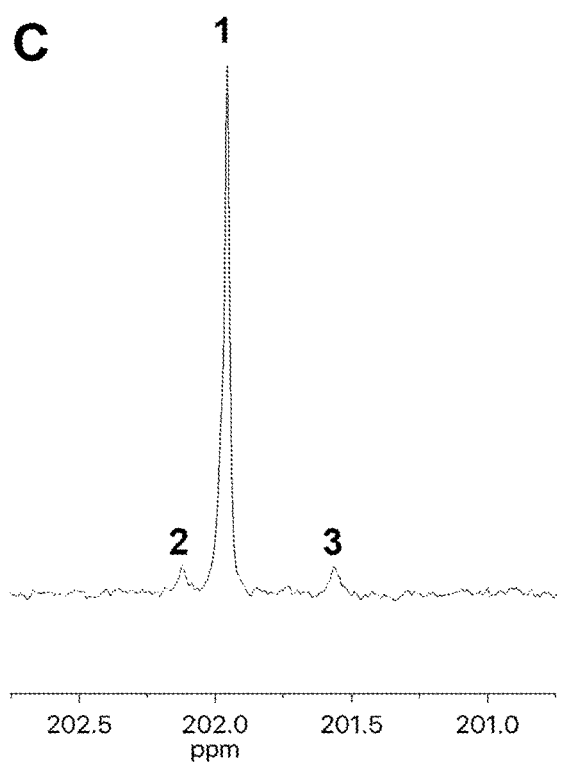
Figure 3:
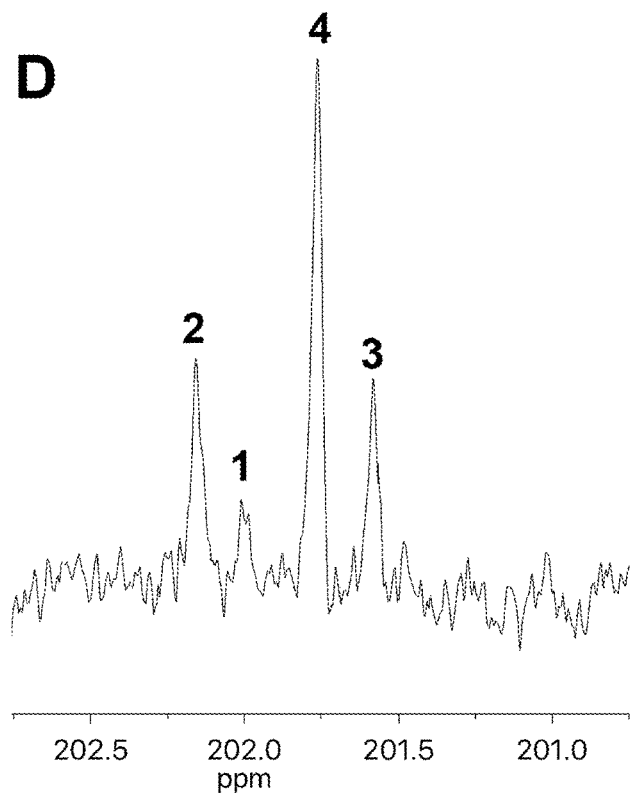

Stereomicrostructures and stereocontrol mechanism. One critical observation and clue to the origin of stereoselectivity is the appearance of four $^{13}$C peaks in the carbonyl region of lower $T_m$ (less stereoregular) PBTL materials (FIG. 3). Considering that only one of the four peaks (at 202.0 ppm) appears in the highest tacticity (100%) and $T_m$ (213° C.) sample, we attribute the other three peaks (202.2, 201.8, and 201.6 ppm) to stereoerrors. Next, to formulate any reasonable explanation for the observation of only four peaks, we make a critical assumption that these carbonyl $^{13}$C signals must be diads, not triads. For diads, there should be 16 possible stereochemical outcomes (2$^4$), or 8 pairs of observable enantiomers with distinct chemical shifts. Therefore, there must be a chemical explanation for the exclusion of four other pairs of enantiomers. All 8 possible diastereomers (their enantiomers not shown) at the diad level are shown in Scheme 2, which are broken into two sets (I and II) of four. Diastereomers 1 and 5 represent the two possible parent enantiomers that arise from inherent chain-end stereoselectivity inherited from the unracemized enantiomeric cis-monomer. It makes sense to split them up into these two scenarios if, and only if, the chiral center adjacent to the sulfur does not racemize (note that in each set, the stereocenters adjacent to the sulfur atom do not change). Regardless of what the parent chirality is, cis/cis threodisyndiotactic 1 [(R,S)(S,R)] or cis/cis threodiisotactic 5 [(R,S)(R,S)], we can still infer that racemization between any of the diastereomers in scenario I to scenario II requires a flip in chirality at one of the stereocenters adjacent to a sulfur. Therefore, under the above assumption we can consider the two scenarios mutually exclusive, and thus provide a well-reasoned chemical explanation for the exclusion of the four statistically possible, but missing peaks. To understand which scenario can be ruled out, we performed density-functional theory (DFT) calculations and reported relative energies of the 8 diads in Scheme 2. From a thermodynamic perspective, group I diastereomers are calculated to be more stable than the ones in group II. Specifically, threodisyndiotactic 1, representing the tacticity formed by the stereoselective chain-growth, is about 2 kcal/mol more stable than threodiisotactic 5 and, among the racemized chains, trans/trans 4 is the favored one. The kinetic results that emerged from DFT analysis of mechanistic pathways discussed below show that the selective formation of 1 is also kinetically favored.

Scheme 2. Structures of all possible stereo-arrangements (tacticities) in diads (enantiomers not shown) and DFT calculated relative energies (numbers in kcal/mol).

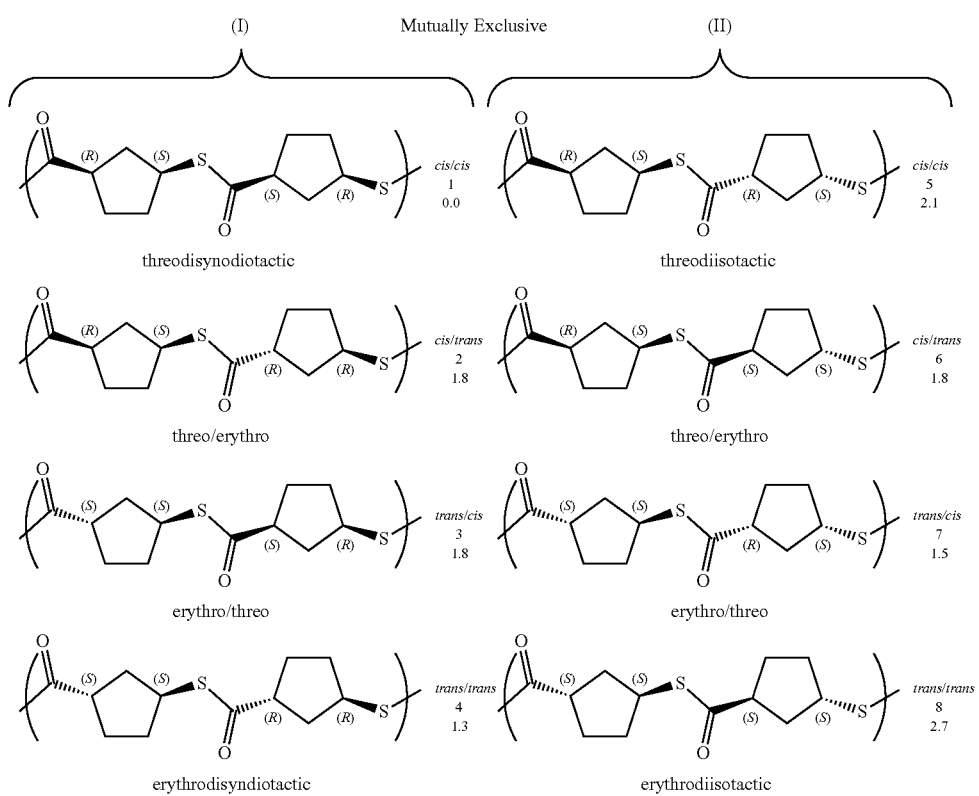

The above rationalization can also explain the two outside peaks (202.2 and 201.6 ppm), which are stereoerrors, that apparently always have similar integration (FIG. 3B-D). There are two cis/trans diastereomers, 2 and 3. Since each $^{13}C$ peak is representing one specific carbonyl carbon that can either be on the cis ring or the trans ring within the cis/trans diad, and since these are two chemically different carbons, they would logically be similar in abundance and therefore have similar integration in every case. Lastly, the inside/right peak (4) represents the trans/trans diastereomer. This assignment is consistent with FIG. 3D for the PBTL produced by $^{t}Bu-P_4$ under more dilute conditions, where the trans/trans peak is highest in intensity due to facile racemization under such conditions.

We propose a stereospecific chain-end control mechanism based on inherent steric differences in the pro-(S) and pro-(R) faces of any incoming $^{[221]}BTL$ molecule, coupled with the chirality of any propagating PBTL anionic chain end. Stereomistakes are caused by racemization of the stereocenter α- to a PBTL carbonyl by an equivalent of free base. And while one might expect stronger bases to produce more stereoerrors, the results from Table 1 indicated that stronger bases are actually the most stereoselective. This counter-intuitive observation can be explained by the absolute concentration of the free base being lower in the case of a stronger base such as $^{t}Bu-P_4$ in comparison to a weaker base such as DBU. This hypothesis is also supported by the higher $T_m$'s observed at higher [M]/[B:] ratios, where the absolute concentration of the free base must be lower. However, current evidence could not allow us to conclusively rule out an alternative hypothesis that the higher stereoselectivity achieved by the stronger base $^{t}Bu-P_4$ is due, at least partially, to its much greater steric hindrance (thus bulkier resulting conjugate-acid anion). Deconvolution of the steric bulk from the basicity of bases requires further structure/reactivity studies. Overall, the experimental observations and analyses led to three critical conclusions: (1) the thiolate anion is not a strong enough base to racemize the α-carbonyl carbon; (2) the proton adjacent to the sulfur is not acidic enough to racemize; and (3) stronger bases are less prone to racemize the polymer chain because they are more likely to exist in the innocuous protonated form.

To address the above mechanistic hypotheses, DFT calculations were carried out for the ROP of racemic $^{[221]}BTL$ with $^{t}Bu-P_4$. Starting from the anionic thiolate propagating chain A stabilized by electrostatic interaction with the protonated base [BH]⁺ (Scheme 3A), the next monomer addition occurs through a nucleophilic attack by the thiolate on the carbonyl of the monomer with concomitant ring opening and reformation of a longer thiolate chain. The reaction of the pro-(S) face of $^{[221]}BTL$ requires a barrier of only 8.5 kcal/mol, 4.6 kcal/mol lower than that for the pro-(R) face, confirming a completely stereospecific chain-end control. Moreover, this kinetic barrier difference shows that the selective formation of diad 1 [(R,S)(S,R)] over 5 [(R,S)(R,S)] is both kinetically and thermodynamically favored.

Next, we investigated the possible pathways leading to stereoerrors. The proton exchange between the thiolate anion at the chain-end and the base creates an equilibrium between ion pair A and neutral thiol+base pair B (Scheme 3A). As expected, the formation of B is disfavored but, when formed, B can facilitate racemization at the α-carbonyl carbon through abstraction of the proton by the released base, which has a barrier of 13 kcal/mol leading to C (only 3.6 kcal/mol higher in energy than B). On the other hand, analogous product D, generated by racemization at the stereocenter adjacent to sulfur, is very high in energy (41.4 kcal/mol higher than A, or 28.4 kcal/mol higher than B); thus, its formation can be ruled out. Further chain growth from C occurs more rapidly for the newly formed trans chain-end that propagates with a barrier lower by almost 2 kcal/mol with respect to the regular chain-end. These results support the formation of a predominantly trans/trans structure (4 in Scheme 2), and its existence as a kinetic product when the reaction conditions were employed such that extensive racemization can occur (FIG. 3D).

Furthermore, we examined both initiation and propagation pathways for the IMes-catalyzed cyclic PBTL formation in toluene (Scheme 3B). The initiating nucleophilic attack of IMes to the carbonyl carbon of [221]BTL requires a barrier of 12.6 kcal/mol, leading to ring-opened zwitterionic adduct E that is 6.6 kcal/mol higher in energy than the reactants. The following monomer addition is also stereoselective ($\Delta\Delta G^{\neq}$ of 2.5 kcal/mol between the transition states for the two faces of the monomer) with a relative energy barrier of 16.3 kcal/mol for the favored enantiomer which also leads to the thermodynamically favored diad (threodisyndiotactic P-1). The propagation step for the favored stereoselective pathway requires a relative energy barrier of 11.9 kcal/mol for the addition of the third monomer (Scheme 4A). The lower energy required in this step with respect to the previous one correlates well with the strength of the ion-pair formed by the growing chain. Indeed, in the initial adduct E the end-to-end distance is very short, i.e. 2.10 Å, indicating a very tight ion-pair, but after at least two monomer units have been inserted into the chain, the ion-pair is much weaker with an end-to-end distance of 2.88 Å.

Scheme 3B. Proposed stereospecific ROP mechanism. Zwitterionic initiation, propagation, chain extension, and cyclization fundamental steps for cyclic PBTL formation by IMes. DFT calculated relative free energies in toluene (kcal/mol), and $\Delta G^{\neq}$ calculated as the free energy difference between each transition state and its preceding minima.

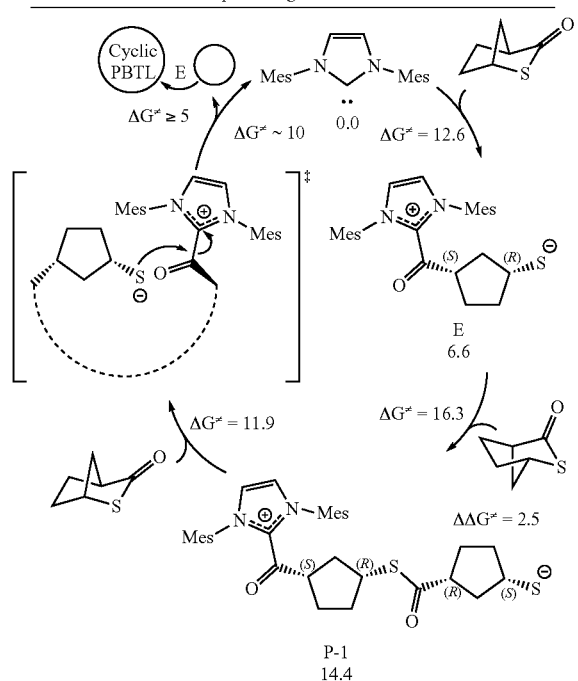

Scheme 3A. Proposed stereospecific ROP mechanism. Stereospecific ROP of [221]BTL into perfectly stereoregular linear PBTL (P-1) with threo-disyndiotacticity by chain-end control (top) and stereoerror formation via racemization at the stereocenter adjacent to the carbonyl by free base present in the system (bottom).

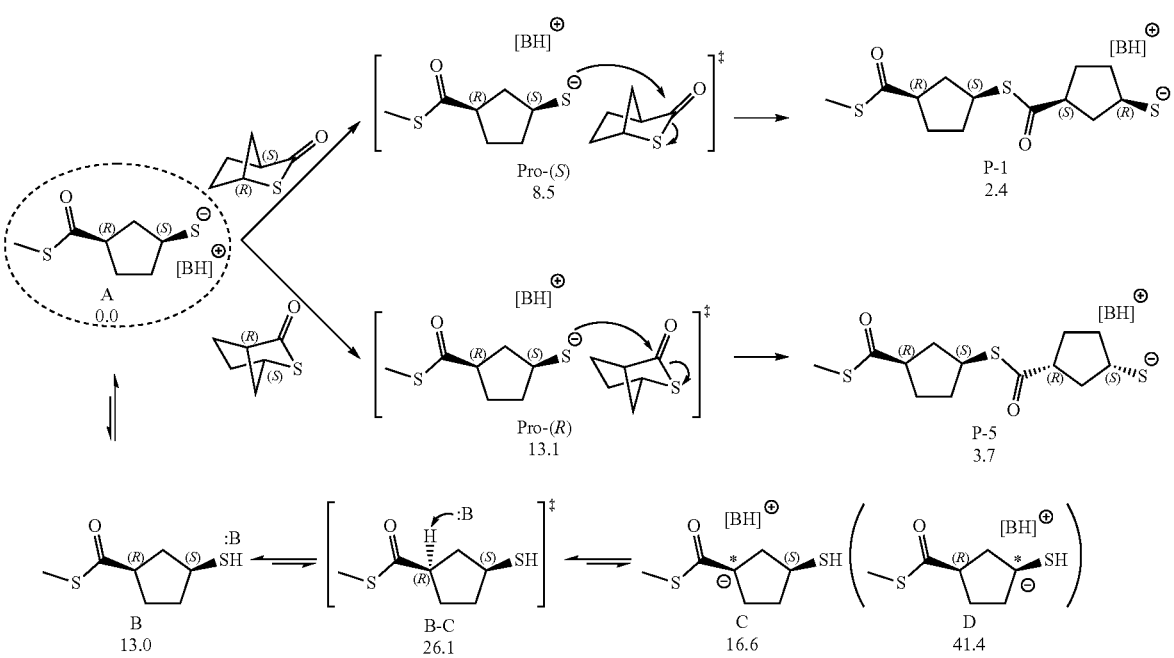

A complete chain propagation scenario contemplates also possible intermolecular chain transfer by coupling of two growing chains and regeneration of the catalyst with an energy barrier of only 9.9 kcal/mol (Scheme 4B). The "truncated" model used, which is based on a hypothesis that there is no ring strain for big rings, allows one to ignore the repeat units and compute only the reaction between the two chain ends to avoid the conformational issues caused from the modeling of long chains. This chain transfer step competes with the analogue intramolecular cyclization step that is approximated to have a similarly low energy barrier since the same "truncated" model can be used to model the chemistry of both the chain transfer reactions. Finally, we considered the possible reactivation of small rings by active propagating species E or its homologs to test the possibility for cyclized chains to reenter the propagation cycle and lead to a further increase of MW (Scheme 4C). Considering a ring formed by two monomer units, the energy barrier required for the propagating chain to reopen the ring by E amounts to only 5 kcal/mol (which will increase as the ring size increases), supporting the facile formation of high MW chains even when there are small rings formed during the initial stage of polymerization. Thus, the lack of control and high MW/Đ can be understood as a broad probability distribution encompassing inter/intra molecular chain transfer and macrocyclic ring-opening/ring-closing.

Scheme 4. Proposed chain growth, transfer, and reactivation mechanisms in the ROP of [221]BTL by IMES. (A), General chain growth step following the initiation step. (B), Intermolcecular chain transfer by coupling of two growing chains and regeneration of the IMes catalyst. (C), Reactivation of small rings (represented by the smallest possible ring) by active propagating species for cyclized chains to reenter the propagation cycle and lead to a further increase of the MW. DFT calculated energy barriers (ΔG$^{\ne}$) in toluene (kcal/mol) reported as the free energy difference between each transition state and its preceding minima.

A. General chain growth step

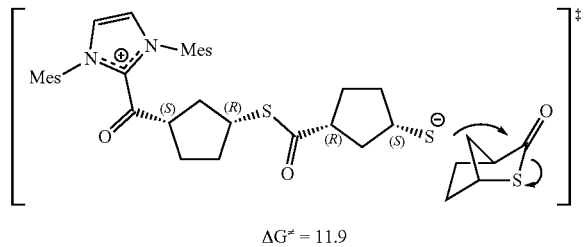

$\Delta G^{\ne} = 11.9$

B. General china transfer step

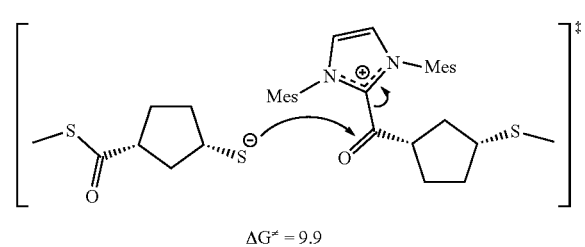

$\Delta G^{\ne} = 9.9$

C. General ring reactivation step

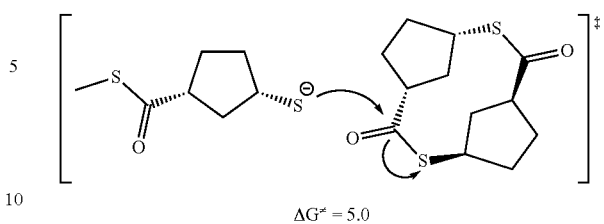

$\Delta G^{\ne} = 5.0$

Lastly, we also compared the computed ΔΔG$^{\ne}$ values in toluene and dimethylformamide (DMF) for the monomer addition step (E to P-1, Scheme 3B). The calculated ΔΔG$^{\ne}$ value between the two competing transition states was reduced from 2.5 kcal/mol in toluene to only 1.2 kcal/mol in DMF, in agreement with the low stereo selectivity observed in DMF experimentally. More interesting, we noticed that the stereoselection is inverted with the chain preferring to select the monomer of the opposite chirality in DMF than in toluene. Looking closely to the geometries of the two transition states, it emerges that the structure having the shorter distance between the positively and the negatively charged chain-ends (i.e. the tighter ion pair) is strongly favored in an apolar solvent such as toluene, but this tight ion pairing becomes disfavored in a polar solvent such as DMF where the solvent-chain-end interactions are stronger and compete with the in-chain interactions.

Figure 4:
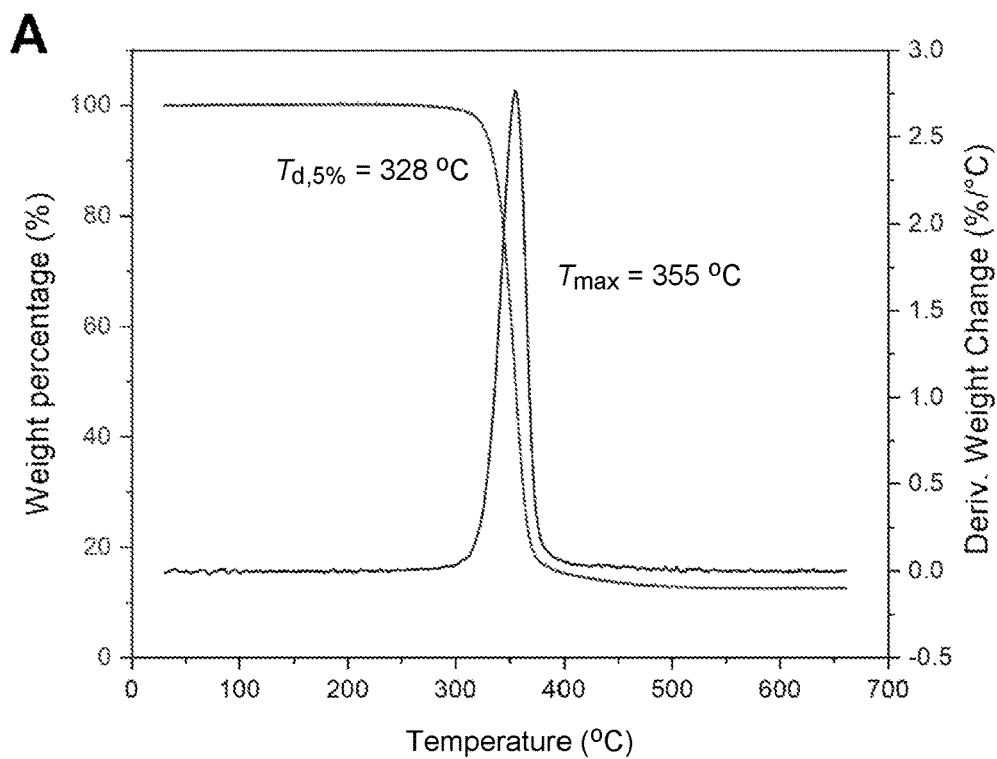
FIG. 4. Thermal and mechanical properties as well as intrinsic crystallinity and recyclability. (A), TGA curves of cyclic PBTL. (B), Stress-strain curves for PBTL$_{178}$ ($T_m$=178° C., $M_n$=9.87×10$^4$ g mol$^{-1}$) and PBTL$_{189}$ ($T_m$=189° C., $M_n$=2.28×10$^5$ g mol$^{-1}$). (C), $T_m$ values as a function of tacticity for the cyclic PBTL materials produced by IMes. (D), Correlation between $T_m$ and tacticity values for the cyclic PBTL materials produced by IMes in the linear region. (E), Overlays of $^1$H NMR spectra (25° C., CDCl$_3$, residual solvent peaks at 7.26 and 1.56 ppm for CHCl$_3$ and H$_2$O, respectively): (1), cyclic PBTL before depolymerization; (2) the colorless solid product recovered after depolymerization (sublimation setup with La—N catalyst at 100° C. for 24 h); (3) pure starting $^{[221]}$BTL for comparison.
Figure 4:
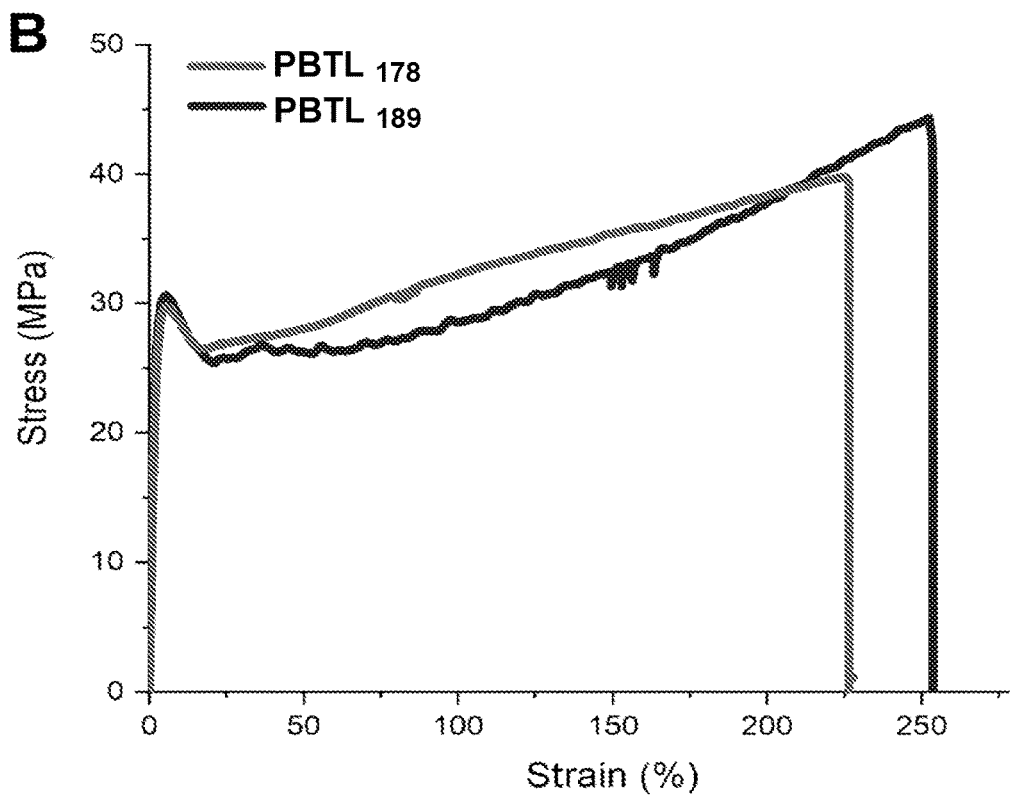
Figure 4:
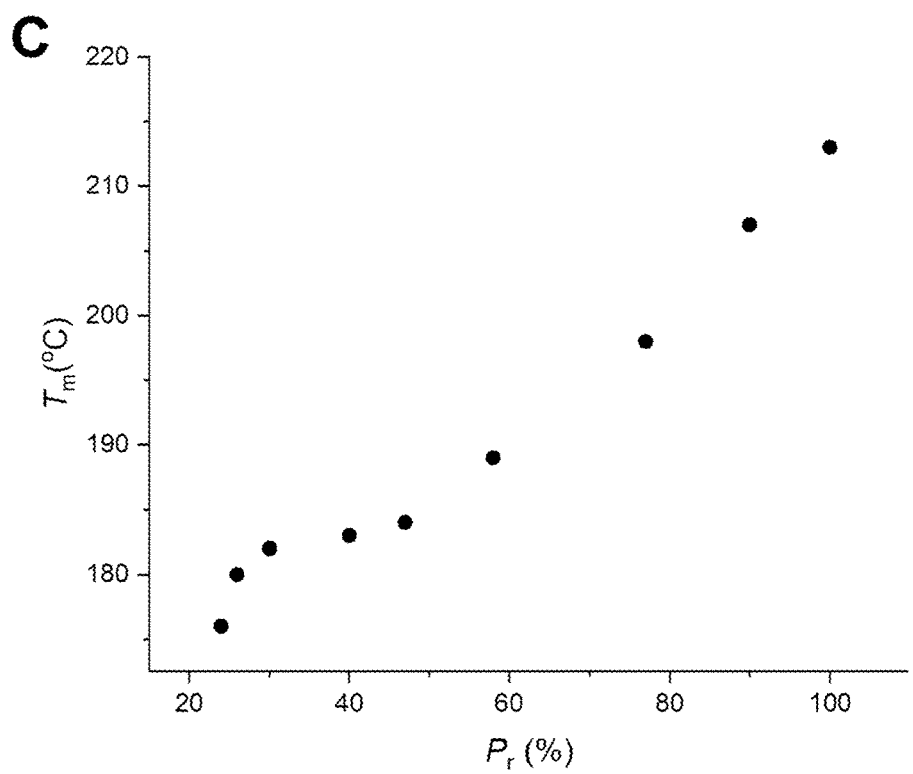
Figure 4:
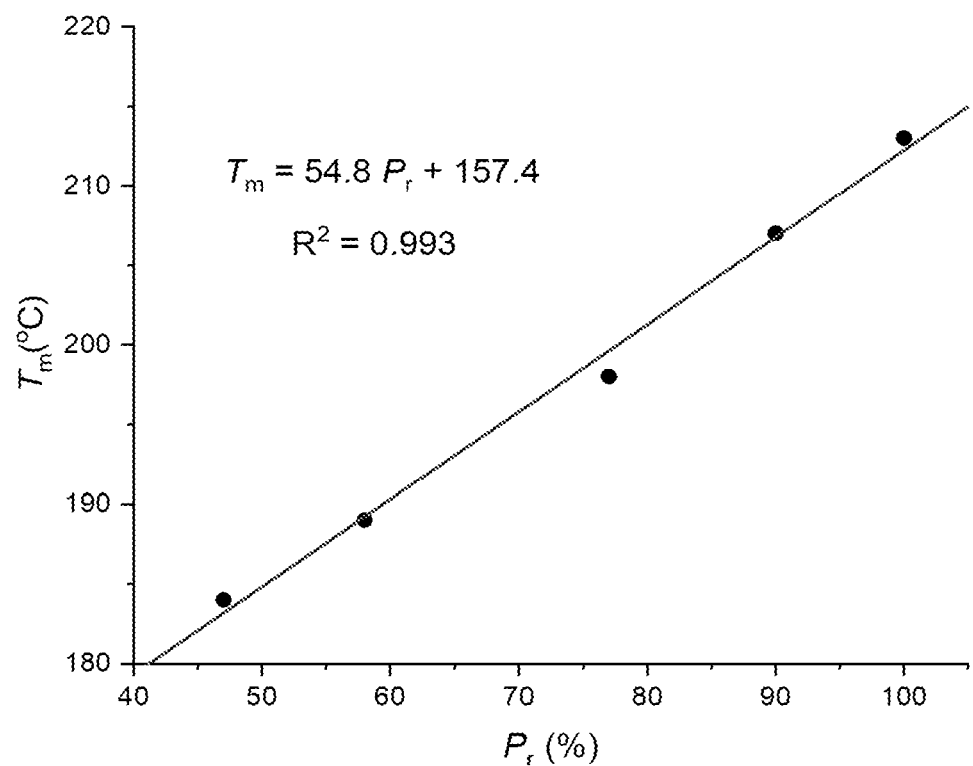
Figure 4:
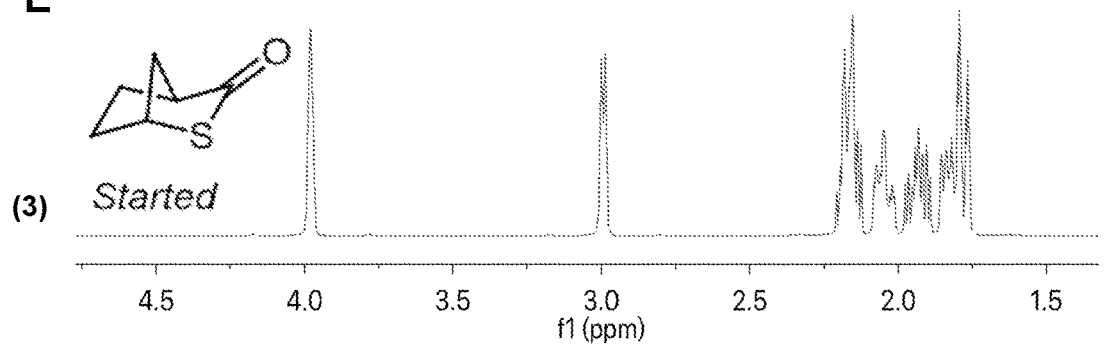
Figure 4:
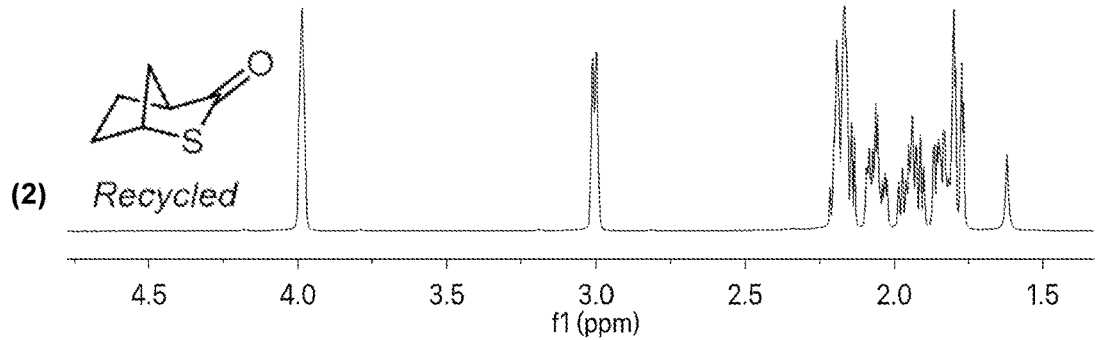
Figure 4:
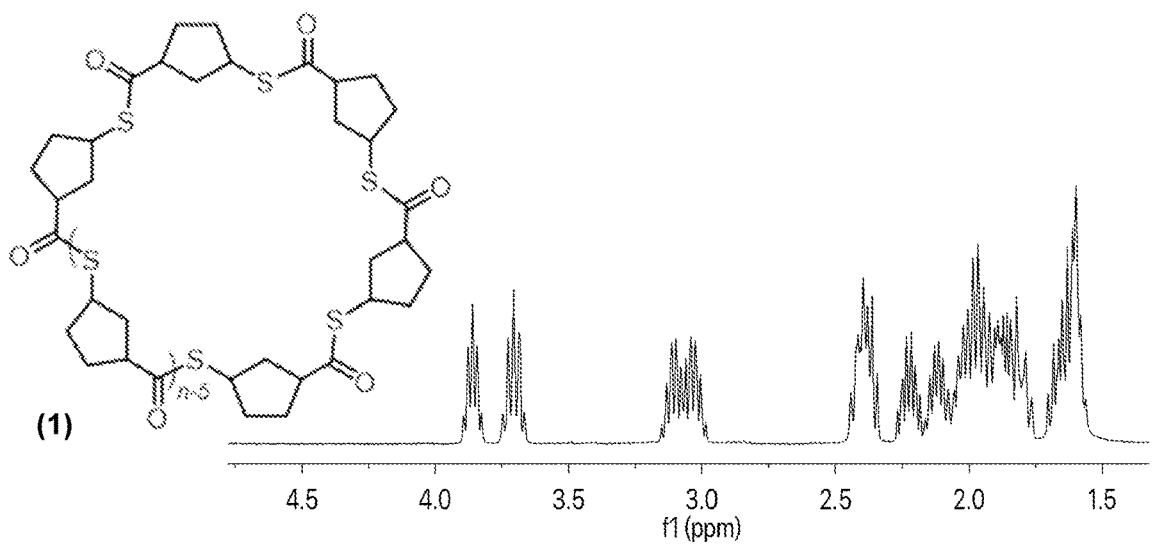
Figure 5:
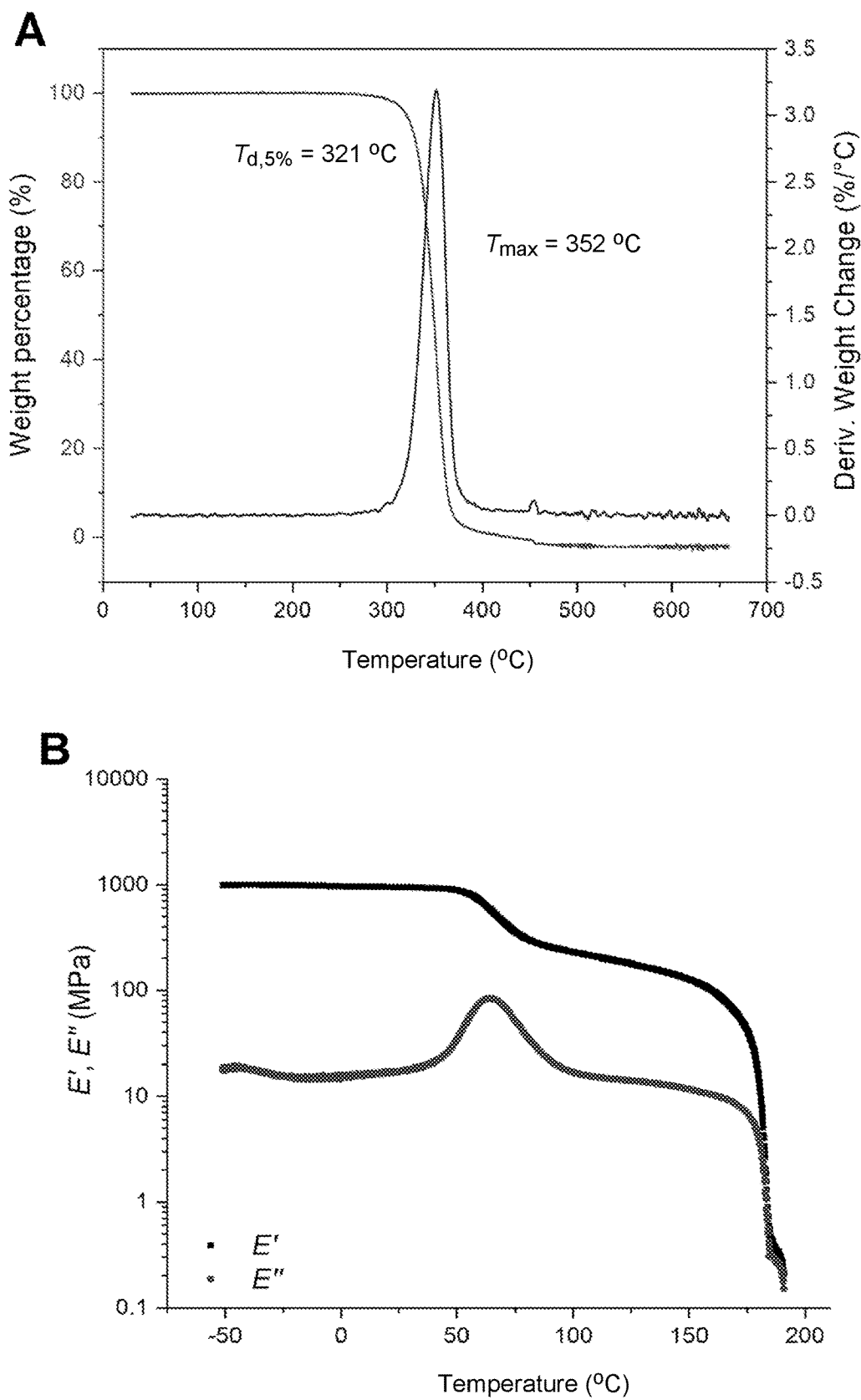
FIG. 5. Thermal, thermomechanical, and spectroscopic properties. (A), TGA curves of linear PBTL. (B), Overlays of storage modulus E' and loss modulus E" for PBTL$_{178}$ measured by DMA (tension film mode, 0.3% strain, 1 Hz, 3° C. min$^{-1}$). (C), Powder XRD profiles of cyclic PBTL$_{183}$, PBTL$_{207}$ and PBTL$_{213}$. (D), Overlays of FTIR spectra of cyclic PBTL$_{183}$, PBTL$_{207}$ and PBTL$_{213}$ in the carbonyl stretching region (str=stretching frequency).
Figure 5:
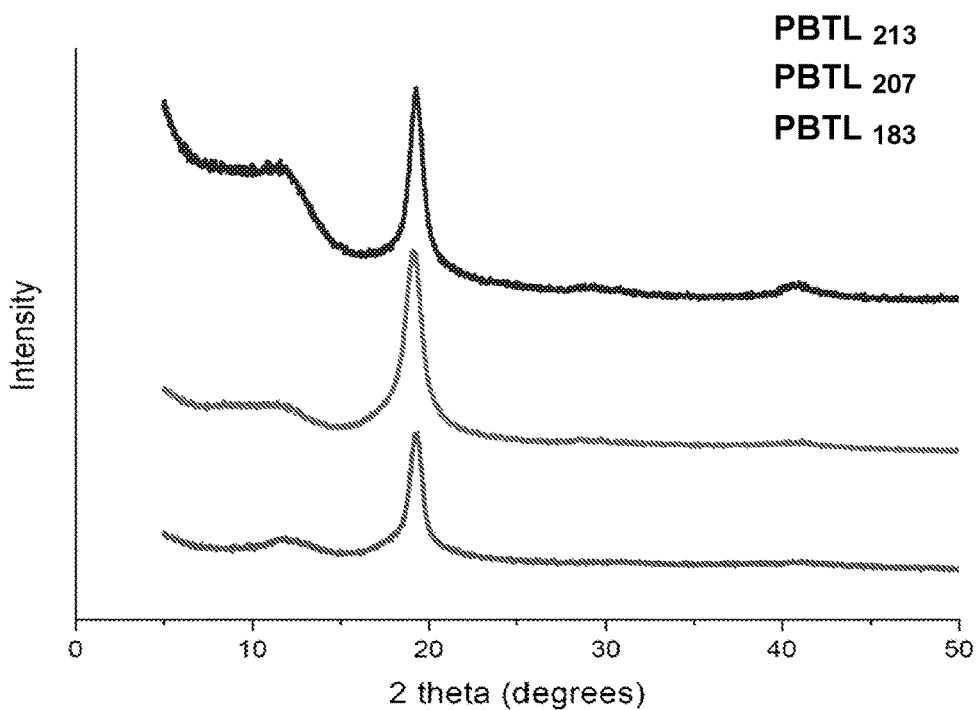
Figure 5:
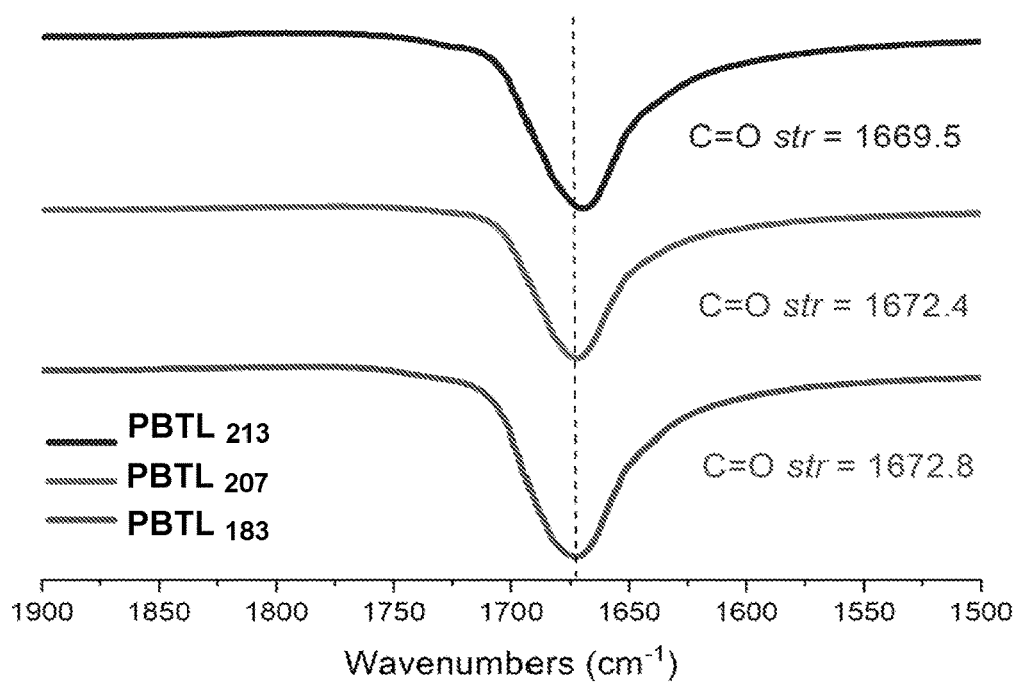

Materials properties of PBTL of varying topology and tacticity. The thermal stability of linear and cyclic PBTL materials were examined by thermogravimetric analysis (TGA) for their $T_{d,5\%}$ and $T_{max}$ (a maximum rate decomposition temperature) values. Both linear and cyclic PBTL materials exhibit high thermal stability, with $T_{d,5\%}>320°$ C., with cyclic PBTL (absent of chain ends) showing somewhat higher $T_{d,5\%}$ than the linear PBTL. For example, cyclic PBTL produced by IMes alone was analyzed to have $T_{d,5\%}=328°$ C. (FIG. 4A), which is 7° C. higher than the linear PBTL obtained with [$^t$Bu-P$_4$+BnOH] (FIG. 5A).

Mechanical properties of crystalline cyclic PBTL materials with two different $T_m$ values (different tacticities) prepared from the ROP of racemic [221]BTL by IMes at a multi-gram scale were examined by tensile testing. Dog-bone-shaped specimens of PBTL$_{178}$ (subscripted 178 denotes its $T_m$ value of 178° C.; $M_n$=9.87×10$^4$ g mol$^{-1}$) and PBTL$_{189}$ ($M_n$=2.28×10$^5$ g mol$^{-1}$) were prepared by solvent-casting, followed by extensive drying in open air and a heated vacuum oven at 100° C. Despite being highly crystalline with high $T_m$ values, both polythioesters are ductile, with elongation at break reaching greater than 200%: 222±5% for PBTL$_{178}$, 233±22% for PBTL$_{189}$ (FIG. 4B). They are also hard and strong materials, with high Young's modulus and ultimate tensile strength of E=2.00±0.18 GPa and $\sigma_B$=41.4±3.0 MPa for PBTL$_{189}$, and E=1.38±0.17 GPa and $\sigma_B$=36.3±3.5 MPa for PBTL$_{178}$. Overall, they can be characterized as hard, strong, ductile and tough plastics, with PBTL of the higher MW and $T_m$ outperforming the one with lower values.

Applying different annealing temperatures provides another strategy to modulate the properties of PBTL to meet different application demands. For example, annealing the above specimens at 140° C., which is higher than their crystallization temperatures (~130° C.), yielded different mechanical properties. Specifically, PBTL$_{189}$, when annealed at 140° C., resulted in a material with ~40% higher Young's modulus (E=2.79±0.16 GPa) and ~19% higher tensile strength ($\sigma_B$=49.1±3.0 MPa) compared to the material annealed at 100° C. DSC measurements of the PBTL sample before and after the annealing showed that, after the annealing, the heat fusion from the first heating scans was enhanced by 8.4 J/g and the transition for $T_g$ also became obscure, both observations of which point to an increase in crystallinity after annealing.

Thermomechanical properties of two PBTL samples with $T_m$=178° C. ($M_n$=9.87×10$^4$ g mol$^{-1}$) and $T_m$=213° C. ($M_n$=3.33×10$^4$ g mol$^{-1}$) were examined by dynamic mechanical analysis (DMA) in a tension film mode. The thermomechanical spectra of $PBTL_{178}$ (FIG. 5B) and $PBTL_{213}$ show that both samples exhibited a high storage modulus (E') at RT, although E' (1.08±0.14 GPa) of $PBTL_{213}$ is somewhat higher than that (0.93±0.06 GPa) of $PBTL_{178}$. On the other hand, E' of both materials only decreased by about one order of magnitude after $T_g$, and the materials still maintained a high E' in the rubbery plateau until reaching a flow temperature of above their $T_m$ values, characteristic of a semi-crystalline material. The α-transition temperature, given by the maximum value of tan(δ) (the loss modulus/storage modulus ratio, E"/E') measured by DMA was 68° C. for $PBTL_{178}$ and 98° C. for $PBTL_{213}$, which is lower than the $T_g$ (112° C. for $PBTL_{213}$) measured by DSC.

Powder X-ray diffraction (pXRD) profiles of the cyclic PBTL with varying tacticities as reflected by different $T_m$ values were also obtained. The main diffraction peak of each PBTL sample was similar, appearing at 2θ of 19.1°, corresponding to a d spacing of 4.6 nm. With increasing the tacticity from $PBTL_{183}$ to $PBTL_{207}$ to $PBTL_{213}$ with perfect tacticity, the minor diffraction peak at 11.7° grows gradually (FIG. 5C), and both peaks become somewhat sharper, consistent with increasing the crystallinity and $T_m$ values. Overlays of Fourier transform infrared (FTIR) spectra in the carbonyl stretching region of these three PBTL samples (FIG. 5D) revealed a red shift of the C=O stretching frequency ($v_{C=O}$) for the perfectly tactic $PBTL_{213}$ to a wavenumber 3 cm$^{-1}$ lower than that for the lower tactic PBTL samples.

Intrinsic crystallinity and chemical recyclability. A remarkable feature of the PBTL material is its intrinsic crystallinity, exhibiting a high $T_m$ ranging from the lowest 166° C. to the highest 213° C., regardless of topology (linear or cyclic) or tacticity (from low 20% to perfect 100%). It is worth noting here that the tacticity further modulates the crystallinity, as shown by the dependence of $T_m$ values on tacticity. Taking the cyclic PBTL material as an example, a plot of $T_m$ vs. tacticity displays an overall upward trend (FIG. 4C), and there shows an apparent linear correlation after the tacticity reaches about 50% (FIG. 4D), with $T_m$ (° C.)=54.8 $P_r$+157.4 ($R^2$=0.993) and a calculated maximum $T_m$ of 212.2° C. at 100% $P_r$. If all data points (including those with tacticity lower than 50%) are plotted, then the relationship becomes: $T_m$ (° C.)=44.6 $P_r$+165.8 ($R^2$=0.984), giving a calculated minimum $T_m$ of 165.8° C., which can be ascribed to the PBTL's intrinsic crystallinity. Experimentally, considering more than 100 PBTL samples varying in tacticity and $T_m$ values that we have generated throughout this study, the highest and lowest $T_m$ ever observed was consistently 213° C. and 166° C., respectively. These results show that this class of PBTL polymers exhibits the unusual ability to crystallize, even with a high degree of stereochemical disorder.

Another desired property of PBTL materials is their intrinsic chemical recyclability for a closed-loop lifecycle. To quantify the polymerizability of [221]BTL and also guide the PBTL depolymerization conditions, thermodynamics of the [221]BTL polymerization were probed using the polymerization with [M]/[IMes]=100/1 and [M]$_0$=3.0 mol L$^{-1}$ in toluene-d$_8$ via variable temperature NMR. The equilibrium monomer concentration, [M]$_{eq}$, obtained by plotting [M]$_t$ as a function of time until [M] became constant, was measured to be 2.55, 2.07, 1.65, 1.32 and 1.05 mol L$^{-1}$ for 20° C., 10° C., 0° C., –10° C., and –20° C., respectively. The Van't Hoff plot of ln[M]$_{eq}$ vs. 1/T gave a straight line with a slope of –1.69 and an intercept of 6.70, from which thermodynamic parameters were calculated to be ΔH°$_p$=–14.1 kJ·mol$^{-1}$ and ΔS°$_p$=–55.7 J·mol$^{-1}$K$^{-1}$. The ceiling temperature ($T_c$) was calculated to be 253 K (–20° C.) at [M]$_0$=1.0 mol L$^{-1}$, or 385 K (112° C.) at [M]$_0$=10.0 mol L$^{-1}$.

The chemical recyclability of PBTL was examined by both bulk and solution depolymerization methods. First, we employed bulk depolymerization at 100° C. in the presence of a catalytic amount of La—N via a sublimation setup. PBTL depolymerized cleanly into pure monomer [221]BTL with >90% isolated yield after in 24 h (FIG. 4E). Next, according to the above obtained thermodynamic parameters, $T_c$=303 K (30° C.) at [M]$_0$=3.0 mol L$^{-1}$ and $T_c$=282 K (9° C.) at [M]$_0$=2.0 mol L$^{-1}$, we investigated solution depolymerization at RT with a catalyst. When PBTL was mixed with IMes (2.3 wt %) in toluene (2.0 mol L$^{-1}$) at RT, after 10 min PBTL depolymerized quantitatively into pure monomer [221]BTL based on $^1$H NMR in toluene-d$_8$. The depolymerization at gram-scale was also successfully carried out. Since [221]BTL exists only in the cis-configuration, it is free of contamination due to absence of possible isomerization. The recycled pure [221]BTL can then be directly re-polymerized into PBTL (run 5, Table 1), thereby demonstrating a closed-loop lifecycle of the PBTL materials.

In summary, we report a new class of polythioester materials derived from the bridged bicyclic [221]BTL, which possess both intrinsic chemical recyclability and crystallinity as well as an unusual set of combined high-performance properties such as high thermal stability, crystallinity, strength, ductility, and toughness. This discovery is significant because accessing such a set of desired properties typically requires composites of materials due to structure/property tradeoffs. Several notable characteristics of the current designer monomer are responsible for its unique polymerization characteristics and performances of its resulting polythioesters: (a) the bridged bicyclic monomer framework increases not only the polymerizability and stereoselectivity but also the chemical recyclability and selectivity due to its enhanced ring strain and the presence of the five-member lactone ring restricted to the cis-configuration; (b) the bridged bicyclic system provides the rigidity in the polymer backbone for enhanced thermal and mechanical properties; and (c) the cyclopentylene rings and sulfur in the polymer render tacticity-independent intrinsic crystallinity.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Materials and Methods

Materials. High-performance liquid chromatography (HPLC)-grade organic solvents were first sparged extensively with nitrogen during filling 20 L solvent reservoirs and then dried by passage through activated alumina [for tetrahydrofuran (THF) and dichloromethane (DCM)] followed by passage through Q-5 supported copper catalyst (for toluene and hexanes) stainless steel columns. HPLC-grade N,N-dimethylformamide (DMF) was degassed and dried over CaH$_2$ overnight, followed by vacuum distillation (CaH$_2$ was removed before distillation). Toluene-d$_8$ was dried over sodium/potassium alloy and vacuum-distilled or filtered, whereas CD$_2$Cl$_2$ and CDCl$_3$ were dried over activated Davison 4 Å molecular sieves.

Organic bases 1-tert-butyl-4,4,4-tris(dimethylamino)-2,2-bis[tris(dimethylamino)-phosphoranylidenamino]-2λ5,4λ5-catenadi (phosphazene) ($^t$Bu-P$_4$, ~0.8 M in hexane), and 1,3-bis(2,4,6-trimethylphenyl)imidazol-2-ylidene (IMes) were purchased from Aldrich Chemical Co. and TCI, respectively, and used as received. Tri[N,N-bis(trimethylsilyl)amide] lanthanum(LII) La[N(SiMe$_3$)$_2$]$_3$ (La—N) was purchased from Aldrich Chemical Co. and used as received. Benzyl alcohol (BnOH) and 1,8-diazabicyclo[5.4.0]undec-7-ene (DBU) were purchased from Fisher Scientific Co. and Aldrich Chemical Co. respectively, which were purified by distillation over CaH$_2$ and stored over activated Davison 4 Å molecular sieves. 3-Cyclopentene-1-carboxylic acid was purchased from Accela Chembio Inc. and used as received, while thioacetic acid, bromotrimethylsilane, and tris(trimethylsilyl)silane were purchased from ACROS Organics and used as received. The monomer was purified and dried by recrystallize in hexanes and sublimation twice prior to polymerization runs and stored in the glovebox for further use.

Figure 6:
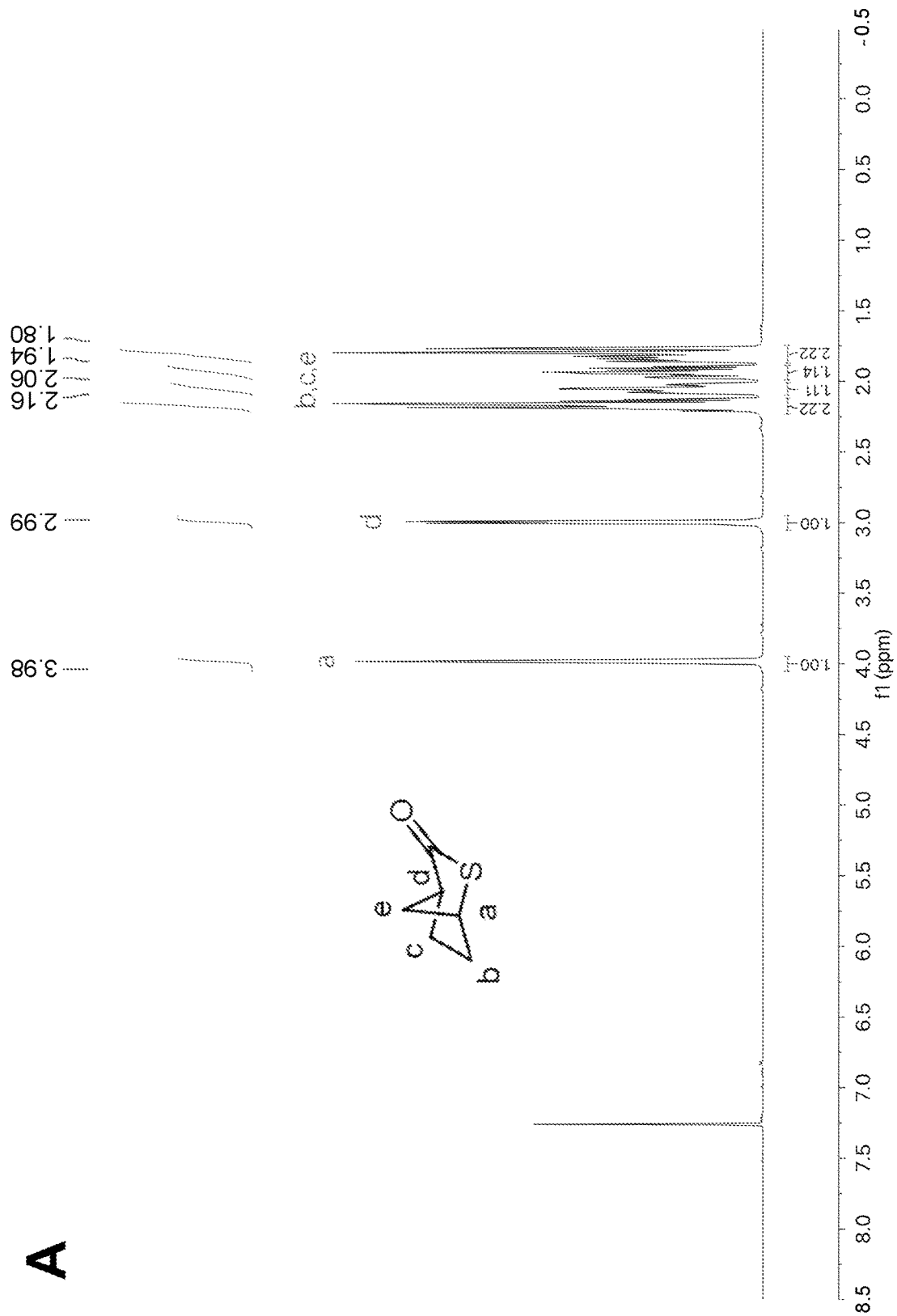
FIG. 6. NMR spectra of monomer. (A), $^1$H NMR (CDCl$_3$, 25° C.) spectrum of $^{[221]}$BTL. (B), $^{13}$C NMR (CDCl$_3$, 25° C.) spectrum of $^{[221]}$BTL.
Figure 6:
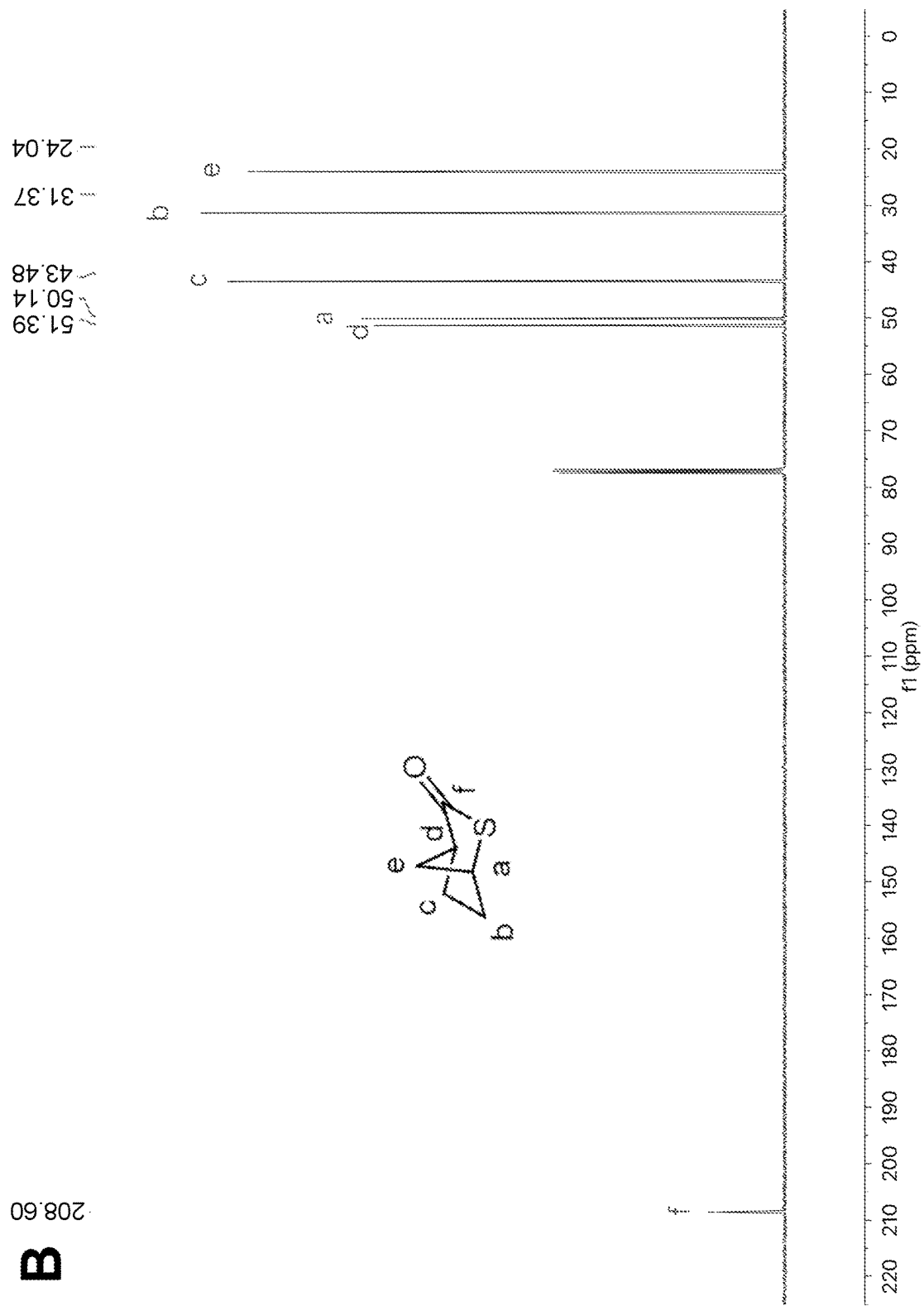

Synthesis of monomer 2-thiabicyclo[2.2.1]heptan-3-one ([221]BTL). The fundamental steps involved in the synthesis of monomer [221]BTL are depicted in Scheme 5. Thioacetic acid (11.9 mL, 170 mmol) was added to 3-cyclopentene-1-carboxylic acid (12.7 g, 113 mmol) at RT. The reaction mixture was heated at 80° C. for 4 h. After cooling to RT, 6.0 M HCl(aq) (100 mL) was added to the reaction mixture and heated at reflux for 12 h. After drying under vacuum, acetic anhydride (20 mL) and trifluoroacetic anhydride (2.0 mL) were added to the reaction mixture, and the mixture was stirred at room temperature for 6 h. After the reaction mixture was concentrated under reduced pressure, 200 mL toluene and para-toluenesulfonic acid (2.1 g, 10%) was added. The reaction mixture was heated to reflux with azeotropic removal of water, using a Dean Stark trap. After 12 h, the reaction mixture was cooled to RT, and the crude product was purified by silica gel column chromatography (1:20 EtOAc/hexanes) to afford pure [221]BTL (11.7 g, 81%) as a white solid (T$_m$=104° C.). The synthesis carried out on a 50-g scale afforded a similar yield. $^1$H NMR (400 MHz, CDCl$_3$), FIG. 6A: δ 3.98 (t, J=3.3 Hz, 1H), 3.00 (dt, J=5.3, 1.6 Hz, 1H), 2.27-2.11 (m, 2H), 2.05 (dddd, J=12.8, 8.9, 4.1, 2.3 Hz, 1H), 2.00-1.88 (m, 1H), 1.87-1.73 (m, 2H). $^{13}$C NMR (101 MHz, CDCl$_3$), FIG. 6B: δ 208.60, 51.39, 50.14, 43.48, 31.37, 24.04.

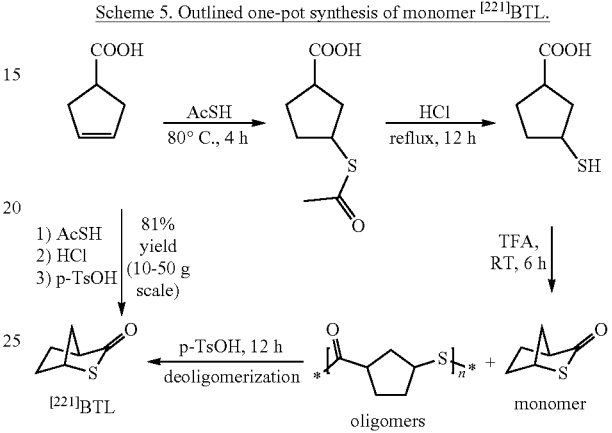

Scheme 5. Outlined one-pot synthesis of monomer [221]BTL.

General polymerization procedures. Polymerizations were performed in 5 mL dried glass reactors inside an inert gas (Ar or N$_2$)-filled glovebox at ambient temperature (~25° C.) runs. In a typical polymerization reaction, the catalyst or initiator was added to the vigorously stirred monomer; when BnOH was used as initiator, it was premixed with the catalyst before adding to monomer. After a desired period of time indicated in the polymerization tables (Table 1 and Table 2), the polymerization was quenched by addition of CHCl$_3$ acidified with benzoic acid (10 mg/mL). The quenched mixture was precipitated into methanol, filtered, and washed with methanol; this procedure was repeated three times to ensure any catalyst residue or unreacted monomer was removed. The polymer was dried in a vacuum oven at 80° C. for 3 days to a constant weight.

TABLE 1

Results of ROP of [221]BTL (M) by different catalyst/initiator systems [a]

| Run | Cat | M (g/mL) | [M]/[Cat] | Time (min) | Conv. [b] (%) | M$_n$ [c] (kg mol$^{-1}$) | Đ [c] (M$_w$/M$_n$) | T$_m$ [d] (° C.) | ΔH$_f$ [d] (J g$^{-1}$) | Tacticity [e] (P$_r$, %) |
|---|---|---|---|---|---|---|---|---|---|---|
| 1 | La—N | 1.60 | 300/1 | 1440 | 57 | 8.8 | 1.54 | 167 | 25.6 | 46 |
| 2 | DBU | 0.80 | 100/1 | 30 | 64 | 12.7 | 1.46 | 166 | 25.1 | 32 |
| 3 | $^t$Bu—P$_4$ | 1.60 | 200/1 | 30 | 74 | 18.6 | 1.54 | 176 | 17.9 | 21 |
| 4 | $^t$Bu—P$_4$ | 2.40 | 1000/1 | 5 | 44 | 49.8 | 1.44 | 213 | 23.5 | 100 |
| 5 | IMes | 3.20 | 1000/1 | 5 | 85 | 115 | 1.75 | 194 | 18.5 | 45 |
| 6 | IMes | 3.20 | 500/1 | 5 | 80 | 74.0 | 1.95 | 182 | 19.0 | 31 |
| 7 | IMes | 1.60 | 100/1 | 5 | 63 | 9.7 | 1.45 | 173 | 25.3 | 20 |
| 8 | IMes | 2.40 | 2000/1 | 30 | 57 | 54.6 | 1.51 | 204 | 20.8 | 88 |
| 9 | IMes | 2.40 | 5000/1 | 30 | 41 | 48.3 | 1.48 | 213 | 25.1 | 100 |

[a] Conditions: conducted in toluene (0.1 mL) at RT with 1 equiv. BnOH relative to organic base catalyst, or 3 equiv. relative to La—N.
[b] Monomer conversions measured by $^1$H NMR spectra of the quenched solution in benzoic acid/chloroform and limited by gelation.
[c] Weight-average molecular weights (M$_w$), number-average molecular weights (M$_n$), and dispersity indices (Đ = M$_w$/M$_n$) determined by gel-permeation chromatography (GPC) at 40° C. in CHCl$_3$ coupled with a DAWN HELEOS II multi-angle light scattering detector and an Optilab TrEX dRI detector for absolute molecular weights.
[d] Thermal transition temperature T$_m$ and heat of fusion ΔH$_f$ measured by differential scanning calorimetry (DSC) with the cooling and second heating rate of 10° C. min$^{-1}$.
[e] Measured by $^{13}$C NMR in the carbonyl region with percentages relative to the cis/cis disyndiotactic peak at 202.0 ppm.

TABLE 2

Results of ROP of [221]BTL (M) catalyzed by IMes [a]

| Run | Solvent | M (g/mL) | [M]/[IMes] | Time (min) | Conv. (%) | $M_n$ (kg mol$^{-1}$) | Đ ($M_w/M_n$) | $T_m$[b] (° C.) | $\Delta H_f$ (J g$^{-1}$) | Tacticity[e] ($P_r$, %) |
|---|---|---|---|---|---|---|---|---|---|---|
| 1 | Tol | 1.60 | 100/1 | 5 | 72 | 66.1 | 2.37 | 176 | 17.6 | 24 |
| 2 | Tol | 1.60 | 300/1 | 3 | 66 | 170 | 2.78 | 180 | 15.8 | 26 |
| 3 | Tol | 2.40 | 300/1 | 3 | 71 | 158 | 2.00 | 184 | 19.7 | 47 |
| 4 | Tol | 2.40 | 600/1 | 5 | 30 | 21.4 | 1.71 | 198 | 25.5 | 77 |
| 5 | Tol | 3.20 | 600/1 | 30 | 33 | 26.2 | 1.40 | 213 | 22.2 | 100 |
| 6 | Tol | 3.20 | 400/1 | 30 | 31 | 126 | 1.47 | 207 | 20.6 | 90 |
| 7 | Tol | 3.20 | 200/1 | 10 | 69 | 110 | 2.15 | 183 | 18.8 | 40 |
| 8 | Tol | 2.40 | 1000/1 | 60 | 43 | 33.3 | 1.45 | 213 | 21.8 | 100 |
| 9 | THF | 3.20 | 1000/1 | 30 | 25 | 74.0 | 1.95 | 213 | 25.8 | 100 |
| 10 | DMF | 3.20 | 600/1 | 5 | 71 | 130 | 2.06 | 182 | 15.5 | 30 |

[a] Conditions: conducted in 0.1 mL of toluene (Tol), tetrahydrofuran (THF), or N,N-dimethylformamide (DMF) at RT by IMes alone. See footnotes under Table 1 for other explanations.
[b] Obtained from DSC 2$^{nd}$ heating scans, except for run 5 from the 1$^{st}$ scan.

Chemical recycling procedures. The chemical recycling experiment was performed in the presence of a catalyst, La[N(SiMe$_3$)$_2$]$_3$. In a glovebox under argon atmosphere, 1.0 g pure cyclic PBTL ($M_n$~100 kg/mol) was added to a sublimator, and La[N(SiMe$_3$)$_2$]$_3$ (1.0 mol %) in 0.5 mL toluene was added. The sublimator was sealed, taken out of the glovebox, and immersed in the oil bath. The mixture was heated at 100° C. for 24 h, after which the reaction mixture was cooled to RT and colorless solid was obtained, which was confirmed to be the cleanly and quantitatively recycled monomer [221]BTL by $^1$H NMR analysis. Gram-scale depolymerization of PBTL was also performed at RT in the presence of an organic base catalyst (IMes). In a glovebox, 1.28 g cyclic PBTL ($M_n$~100 kg/mol) and 4.0 mL toluene was added into a 20 mL vial, and IMes (1.0 mol %) in 1.0 mL toluene was added. The PBTL was completely depolymerized into [221]BTL in 10 min, monitored by $^1$H NMR.

Example 2. Characterization and Analysis

Absolute molecular weight measurements. Measurements of polymer absolute weight-average molecular weight ($M_w$), number-average molecular weight (Me), and molecular weight distributions or dispersity indices (Đ=$M_w/M_n$) were performed via gel-permeation chromatography (GPC). The GPC instrument consisted of an Agilent HPLC system equipped with one guard column and two PLgel 5 μm mixed-C gel permeation columns and coupled with a Wyatt DAWN HELEOS II multi-angle light scattering detector and a Wyatt Optilab TrEX dRI detector; the analysis was performed at 40° C. using chloroform as the eluent at a flow rate of 1.0 mL/min, using Wyatt ASTRA 7.1.2 molecular weight characterization software. The refractive index increments (dn/dc) of the linear and cyclic PBTL were determined to be 0.1638±0.0097 mL/g and 0.1516±0.0061 mL/g, respectively, obtained by batch experiments using Wyatt Optilab TrEX dRI detector and calculated using ASTRA software. Polymer solutions were prepared in chloroform and injected into dRI detector by Harvard Apparatus pump 11 at a flow rate of 0.1 mL/min. A series of known concentrations were injected and the change in refractive index was measured to obtain a plot of change in refractive index versus change in concentration ranging from 0.5 to 5.0 mg/mL. The slope from a linear fitting of the data was the do/dc of the polymer.

Spectroscopic characterizations. The isolated low molecular weight samples were analyzed by matrix-assisted laser desorption/ionization time-of-flight mass spectroscopy (MALDI-TOF MS); the experiment was performed on an Ultraflex MALDI-TOF mass spectrometer (Bruker Daltonics) operated in positive ion, reflector mode using a Nd:YAG laser at 355 nm and 25 kV accelerating voltage. A thin layer of a 1% NaI solution was first deposited on the target plate, followed by 0.6 μl of both sample and matrix (dithranol, 10 mg/mL in 50% ACN, 0.1% TFA). External calibration was done using a peptide calibration mixture (4 to 6 peptides) on a spot adjacent to the sample. The raw data was processed in the FlexAnalysis software (version 2.4, Bruker Daltonics).

X-ray powder patterns of the polymers were obtained with a Thermo Scintag X-2 Powder X-Ray Diffractometer with Cu radiation. Before analysis, specimens were cooled by liquid N$_2$ and grinded until a fine white powder was obtained.

Fourier transform infrared (FT-IR) spectroscopy was performed on a Thermoscientific (Nicolet iS50) FT-IR spectrometer equipped with a diamond attenuated total reflectance (ATR) at RT in the range of 550-4000 cm$^{-1}$.

NMR spectra were recorded on a Varian Inova 400 MHz (FT 400 MHz, $^1$H; 100 MHz, $^{13}$C) or a 500 MHz spectrometer. Chemical shifts for all spectra were referenced to internal solvent resonances and were reported as parts per million relative to SiMe$_4$.

Measurements of thermodynamic parameters. In a glovebox under an argon atmosphere, an NMR tube was charged with IMes (4.56 mg, 0.015 mmol) and 0.2 mL of toluene-d$_8$. The NMR tube was sealed with a Precision Seal rubber septum cap and taken out of the glovebox and immersed in a cooling bath at −78° C. After equilibration at −78° C. for 10 min, [221]BTL (192 mg, 1.5 mmol, [[221]BTL]/[IMes]= 100/1) in toluene-d$_8$ (0.3 mL) was added via a gastight syringe and the NMR tube was brought into a 500 MHz NMR probe precooled to the desired polymerization temperature (20, 10, 0, −10 and −20° C., respectively). The conversion of the monomer was monitored by $^1$H NMR at different time intervals until the conversion remained constant at each temperature. The equilibrium monomer concentration, $[M]_{eq}$, was measured to be 2.55, 2.07, 1.65, 1.32, and 1.05 M for 20° C., 10° C., 0° C., −10° C. and −20° C., respectively. The Van't Hoff plot of $\ln[M]_{eq}$ vs. 1/T gave a straight line with a slope of −1.69 and an intercept of 6.70, from which thermodynamic parameters were calculated to be $\Delta H°_p$=−14.1 kJ·mol$^{-1}$ and $\Delta S°_p$=−55.7 J·mol$^{-1}$K$^{-1}$, based on the equation $\ln[M]_{eq}=\Delta H°_p/RT-\Delta S°_p/R$. The ceiling temperature was calculated $T_c$=−20, 30, 60, and 112° C. at $[M]_0$=1.0, 3.0, 5.0, and 10 mol·L$^{-1}$, respectively, based on the equation $T_c=\Delta H°_p/(\Delta S°_p+R \ln[M]_0)$.

Thermal, mechanical, and rheological analysis. Melting-transition temperature ($T_m$) and glass-transition temperature ($T_g$) of purified and thoroughly dried polymer samples were measured by differential scanning calorimetry (DSC) on an Auto Q20, TA Instrument. All $T_m$ and $T_g$ values were obtained from a second scan (unless indicated otherwise) after the thermal history was removed from the first scan. The second heating rate was 10° C./min and cooling rate was 10° C./min. Decomposition temperatures ($T_{d,5\%}$) and maximum rate decomposition temperatures ($T_{max}$) of the polymers were measured by thermal gravimetric analysis (TGA) on a Q50 TGA Analyzer, TA Instrument. Polymer samples were heated from ambient temperatures to 700° C. at a heating rate of 10° C./min. Values of $T_{max}$ were obtained by the peak values from derivative (wt %/° C.) vs. temperature (° C.) plots, while $T_{d,5\%}$ values were obtained by the temperatures at 5% weight loss from wt % vs. temperature (° C.) plots.

Film specimens suitable for dynamic mechanical analysis (DMA) were prepared via solvent-casting of concentrated polymer solutions in chloroform. Polymer solutions were solvent-cast using a syringe into PTFE molds and left to dry gradually at RT in open air for 24-48 h, then moved to 70° C. oven for 48 h, after which the films were extensively dried in a vacuum oven up to 100° C. or 140° C. for 12 h.

Storage modulus (E'), loss modulus (E"), and tan δ (E"/E') were measured by DMA on a Q800 DMA Analyzer (TA Instruments) in a tension film mode at a maximum strain of 0.3% or 0.05% and a frequency of 1 Hz (complying with strain-sweep and frequency-sweep linearity analysis performed prior to sample testing). Specimens for analysis were generated via solvent-casting of polymer materials in chloroform into PTFE molds (approx. 35×15×1.5 mm), dried, and cut down to a standard width (13 mm). Specimen length (5-10 mm) and thickness (0.40-0.60 mm) were measured for normalization of data by Q-series measurement software (TA Instruments). Test specimens were mounted to screw-tight grips (maximum 2 N). The samples were heated from −50° C. to 250° C. at a heating rate of 3° C. min$^{-1}$. The α-transition temperature was calculated as the peak maxima of the tan δ curve. Samples were tested to the point of yield (amplitude of displacement >20 mm) with measurements repeated for 3 specimens, the values reported are averaged from the measured data.

Tensile stress/strain testing was performed by an Instron 4442 universal testing system (50 N load cell) on dog-bone-shaped test specimens (ASTM D638 standard; Type V) prepared via slow-solvent evaporation. Concentrated polymer solutions in chloroform were solvent cast into PTFE molds (approx. 73×54×7 mm), thoroughly dried, and cut using an ASTM D638-5-IMP cutting die (Qualitest) to standard dimensions. Thickness (0.40-0.60 mm) and grip length (25-26 mm) were measured for normalization of data by the Bluehill measurement software (Instron). Test specimens were affixed into the pneumatic grip (maximum 2 kN) frame at 30 psi ($N_2$). Tensile stress and strain were measured to the point of material break at a grip extension speed of 5.0 mm/min at RT, with the measurements repeated more than 3 times and the values reported are averaged from the measured data.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A polymer comprising a polythioester represented by Formula I:

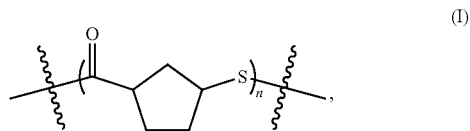

wherein
the polythioester is a linear polythioester or a cyclic polythioester; and
n is 20-50,000.

2. The polymer of claim 1 wherein the polythioester is a linear polythioester.

3. The polymer of claim 1 wherein the polythioester is a tactic polythioester.

4. The polymer of claim 3 wherein the tactic polythioester has at least 20% tacticity.

5. The polymer of claim 3 wherein the tactic polythioester has at least 90% tacticity.

6. The polymer of claim 3 wherein the tactic polythioester comprises diads.

7. The polymer of claim 3 wherein the tactic polythioester consists essentially of diads.

8. The polymer of claim 1 wherein the polythioester of Formula I is represented as Formula IIA, IIB, IIC, or IID:

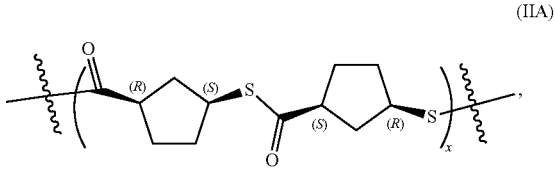

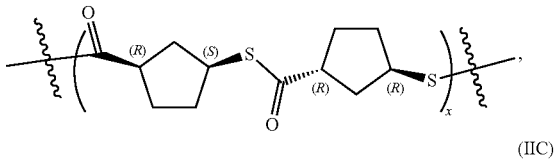

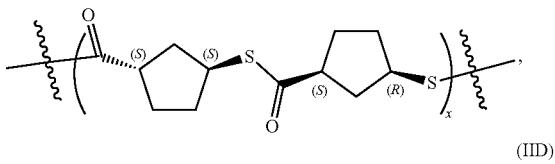

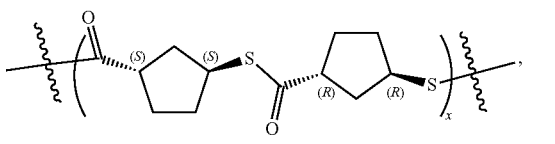

or an enantiomer thereof;
wherein x is 10-25,000.

9. The polymer of claim 8 wherein the polythioester is the threodisyndiotactic polymer of Formula IIA or the erythrodisyndiotactic polymer of Formula IID.

10. A polymer comprising a cyclic polythioester represented as Formula IIIA:

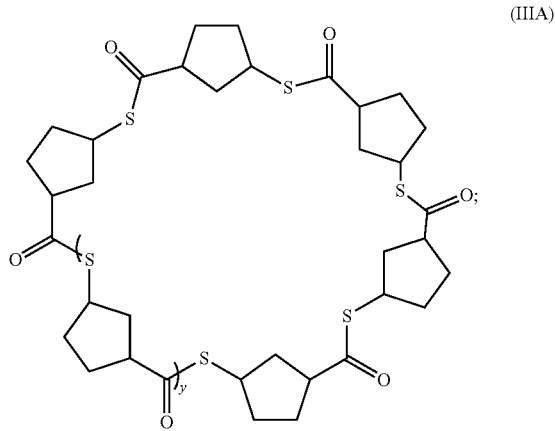

(IIIA)

wherein y is 0-10,000.

11. The polymer of claim 10 wherein the cyclic polythioester of Formula IIIA is represented as Formula IIIB:

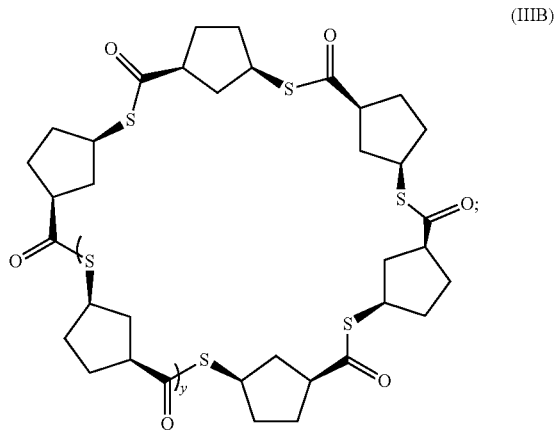

(IIIB)

or an enantiomer thereof.

12. A method for forming the polymer of claim 1 comprising:

a1) contacting a bicyclic thiolactone monomer (M) and catalyst (Cat) to form a cyclic polythioester, wherein the catalyst is a metal-based catalyst or organic N-heterocyclic carbene (NHC); or a2) contacting the bicyclic thiolactone monomer, catalyst, and an initiator to form a linear polythioester, wherein the catalyst is an organic base and the pKa of the organic base is about 12 to about 42;

wherein the monomer undergoes a polymerization reaction; and b) quenching the polymerization reaction in step a1) or step a2);

wherein the ratio of M and Cat expressed as a ratio of their concentrations [M]/[Cat] is about 100/1 or greater, and the polymer is thereby formed.

13. The method of claim 12 wherein the bicyclic thiolactone monomer is 2-thiabicyclo[2.2.1] heptan-3-one ($^{[221]}$BTL).

14. The method of claim 12 wherein the method comprises step a1) and step b) and the catalyst is tris[N,N-bis(trimethylsilyl)amide]lanthanum (III) (La—N) or 1,3-bis(2,4,6-trimethylphenyl) imidazol-2-ylidene (IMes); or the method comprises step a2) and step b) and the catalyst is 1,8-diazabicyclo[5.4.0]undec-7-ene (DBU), tris[N,N-bis(trimethylsilyl)amide]lanthanum (III) (La—N), or 1-tert-butyl-4,4,4-tris(dimethylamino)-2,2-bis[tris(dimethylamino)-phosphoranylid-enamino]-2$\lambda^5$,4$\lambda^5$-catenadi (phosphazene) ($^t$Bu-P$_4$), and the initiator is an alcohol.

15. The method of claim 12 wherein the polymer formed is crystalline and has a melting-transition temperature ($T_m$) of about 150° C. to about 250° C.

16. A method for depolymerizing a polythioester comprising contacting the polythioester according to claim 1 and a catalyst at about 10° C. to about 120° C., wherein the polythioester is depolymerized to the parent bicyclic thiolactone monomer wherein the parent is 2-thiabicyclo[2.2.1] heptan-3-one ($^{[221]}$BTL).

* * * * *